(12) United States Patent
Segal

(10) Patent No.: US 10,031,073 B2
(45) Date of Patent: Jul. 24, 2018

(54) SYSTEM AND METHOD FOR DETECTING COLORED OBJECTS

(71) Applicant: Edo Segal, New York, NY (US)

(72) Inventor: Edo Segal, New York, NY (US)

(*) Notice: Subject to any disclaimer, the term of this patent is extended or adjusted under 35 U.S.C. 154(b) by 0 days.

(21) Appl. No.: 15/364,816

(22) Filed: Nov. 30, 2016

(65) Prior Publication Data

US 2017/0153175 A1 Jun. 1, 2017

Related U.S. Application Data

(60) Provisional application No. 62/261,109, filed on Nov. 30, 2015.

(51) Int. Cl.
| | |
|---|---|
| *G01N 21/25* | (2006.01) |
| *G01N 21/27* | (2006.01) |
| *A63F 9/24* | (2006.01) |
| *A63F 9/00* | (2006.01) |
| *E05B 49/00* | (2006.01) |

(52) U.S. Cl.
CPC .......... *G01N 21/27* (2013.01); *A63F 9/0098* (2013.01); *A63F 9/24* (2013.01); *E05B 49/00* (2013.01); *G01N 21/255* (2013.01); *A63F 2250/24* (2013.01)

(58) Field of Classification Search
CPC .......... G01N 21/27; G01N 21/25; A63F 9/24; A63F 9/00; E05B 49/00; G01J 3/50; G01J 3/51; G01J 3/46; G01J 3/02
See application file for complete search history.

(56) References Cited

U.S. PATENT DOCUMENTS

| | | | |
|---|---|---|---|
| 7,847,942 B1* | 12/2010 | Milford | G01J 3/02 235/469 |
| 2005/0100943 A1* | 5/2005 | Kambara | B01J 19/0046 435/6.12 |
| 2013/0126618 A1* | 5/2013 | Gao | G06K 7/10 235/469 |
| 2015/0062584 A1* | 3/2015 | Hennebelle | G01J 3/50 356/402 |

* cited by examiner

*Primary Examiner* — Abdullahi Nur
(74) *Attorney, Agent, or Firm* — Leason Ellis LLP

(57) ABSTRACT

A system and method for detecting colored objects and decoding messages are provided. A light source is operatively coupled to a power source for emitting light on a colored object. A light receiver is configured to receive the emitted light from the light source as the light reflects off the colored object and is further configured to detect color of the reflected light. Further, a processor is operatively coupled to processor readable media and is configured to receive, via a communications module, information representing the color of the reflected light. A housing is included for supporting the light source, the light receiver, the processor and the communications module. The processor is configured to process the information representing the color of the reflected light and provide at least partial message information corresponding to the color.

18 Claims, 26 Drawing Sheets

ASSEMBLY FOR RECTANGULAR FLAT BEADS

ASSEMBLY FOR RECTANGULAR-FLAT BEADS

ASSEMBLY AND BOX FOR RECTANGULAR-FLAT BEADS

ASSEMBLY FOR RECTANGULAR FLAT BEADS

SCHEMATICS OF THE PRINTED CIRCUIT BOARD

PRINTED CIRCUIT BOARD

PRINTED CIRCUIT BOARD

SYSTEM AND METHOD FOR DETECTING COLORED OBJECTS

CROSS-REFERENCE TO RELATED APPLICATIONS

The present application is based on and claims priority to U.S. Provisional Patent Application 62/261,109, filed Nov. 30, 2015, the entire contents of which is incorporated by reference as if expressly set forth in its respective entirety herein.

FIELD

The present application relates, generally, to gaming and, more particularly, to applications of detecting colored objects and processing information associated therewith.

BACKGROUND OF THE INVENTION

The increasing proliferation of mobile computing devices, such as smartphones, has resulted in users increasingly relying on such devices for recreational purposes, including for game playing. Accordingly, many electronic video games such as multi-player video games have overtaken traditional "physical" games, such as board games, in popularity. While electronic video games may provide many advantages over board games, such video games do not provide the same tangible, "real world" gameplay experience, as reflected in certain board games through the use of figurines or gameplay pieces.

The present application addresses these and other considerations.

SUMMARY

It is with respect to these and other considerations that the present application is presented.

In various implementations, a system and method for detecting colored objects and decoding messages are provided. A light source is operatively coupled to a power source for emitting light on a colored object. A light receiver is configured to receive the emitted light from the light source as the light reflects off the colored object and is further configured to detect color of the reflected light. Further, a processor is operatively coupled to processor readable media and is configured to receive, via a communications module, information representing the color of the reflected light. A housing is included for supporting the light source, the light receiver, the processor and the communications module. The processor is configured to process the information representing the color of the reflected light and provide at least partial message information corresponding to the color.

Other features and advantages of the present application will become apparent from the following description of the invention that refers to the accompanying drawings.

BRIEF DESCRIPTION OF THE DRAWINGS

Further aspects of the present disclosure will be more readily appreciated upon review of the detailed description of its various embodiments, described below, when taken in conjunction with the accompanying drawings, of which.

DETAILED DESCRIPTION OF THE PREFERRED EMBODIMENTS

The present application provides a system and method for interactive gameplay that encourages physical play with digital extended experiences.

In one or more implementations, a system and method are provided for detecting respective colors of objects, such as beads incorporated in a bracelet or other strand, and converting the detected colors to a human readable or recognizable format, such as letters, words phrases, icons, emoticons, images, audio content or the like. The present application includes a plurality of components that, individually and/or in combination, provide a new form of coded messaging. In one or more implementations, the present application is well-suited for toys or entertainment. Although many of the examples and descriptions provided herein relate to a toy or plaything, the present application is suitable for many other purposes, such as education, administration or for virtually any activity in which communicating and/or decoding coded messages is desirable.

Figure 1:
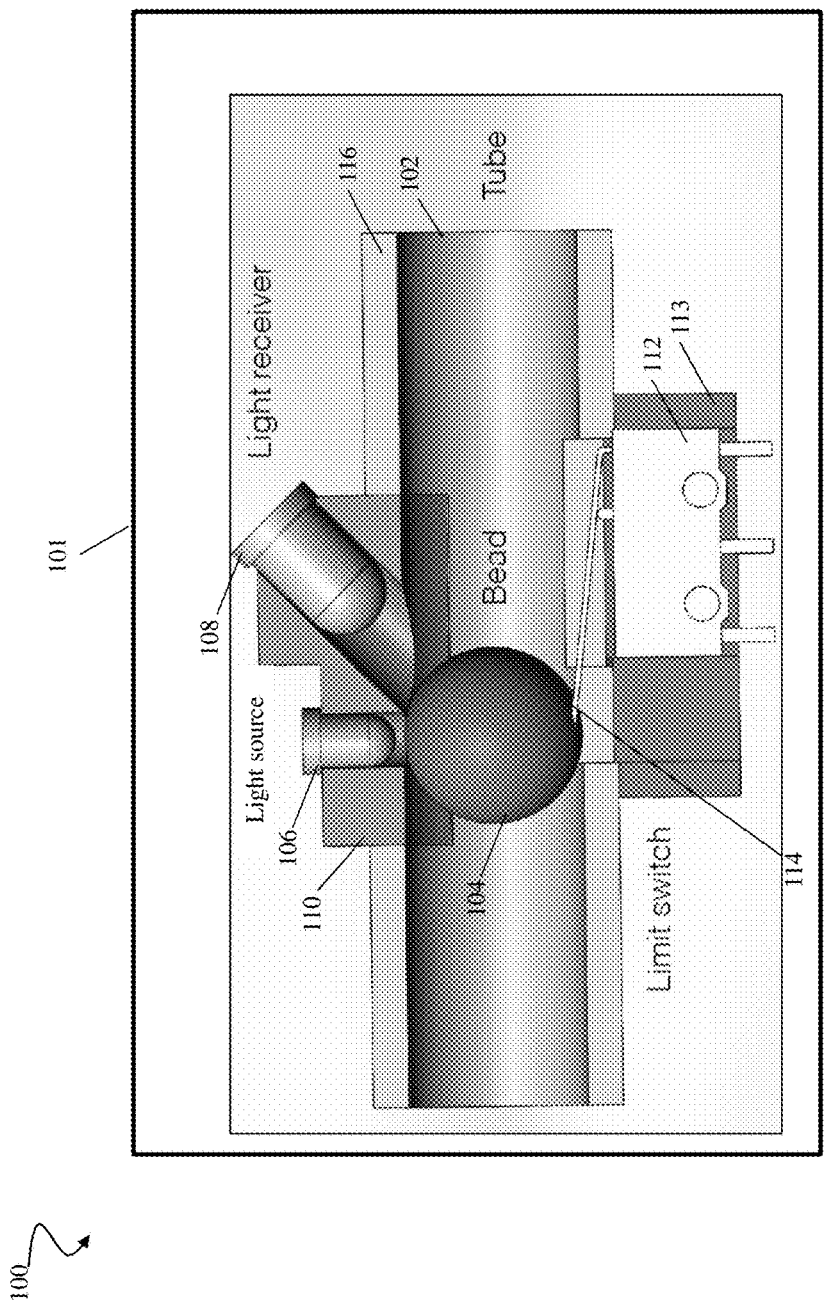
FIG. 1 depicts a colored object detector in accordance with an example implementation of the present application.

Referring now to the drawings, in which like reference numerals refer to like elements, FIG. 1 illustrates an example implementation and depicts a colored object detector 100 that includes components that are incorporated in a housing, such as a box 101. As shown in FIG. 1, a tube 102 is provided and configured to receive bead(s) 104. Bead(s) 104 can be provided with other beads, such as in a strand or other collection, and pass through tube 102 or similar component. Colored object detector 100 is configured to include a light source 106 which, for example, can be a red, green and blue ("RGB") light emitting diode ("LED"), a plurality of individual LEDs or other suitable light sources, and that is configured to emit light on bead 104. Colored object detector 100 is further configured with a light receiver 108, which can be configured to include one or more light sensors, including photodiode(s), photocell(s), photoresistor(s) or other suitable light sensing component(s). In operation, light receiver 108 detects reflected light that is emitted from the light source 106 as the light is reflected from a bead 104 or other suitable object. In one or more implementations, the light source 106 and light receiver 108 are configured within a housing, illustrated and referred to herein, generally, as a sensor block 110. Further, a limit switch 112 can be included for controlling at least light source 106, and can be configured with limit switch well 113.

In an example operation, as bead 104 passes along or through tube 102, the bead 104 makes direct or indirect contact at a point 114 of limit switch 112, which causes the switch 112 to turn on light source 106. As a bead 104 is illuminated by the light source 106, the light receiver 108 detects the light reflected from the bead 104 and can be further configured to detect or otherwise determine the corresponding color of bead 104. In addition to operating to switch the light source 106 on and off, the limit switch 112 can provide for improved stability and/or fixation of bead 104 and, accordingly, improves the ability of the light receiver 108 to detect the color of the bead 104.

In one or more implementations, a tube 102 is configured in or coupled to a tunnel 116 that is positioned to eliminate or at least reduce an amount of ambient light, which further improves the ability of light receiver 108 to sense light reflected from bead 104 and to detect/determine the color of bead 104. Beads 104 configured with similar, though not identical, colors can be respectively detected and distinguished. Detection of colors having subtle distinctions can be made possible as a function of a tunnel through which beads 104 are pulled and/or pushed, and that can be housed in a structure. Configuring detector 100 with a tunnel is particularly useful to reduce or otherwise eliminate ambient or outside light, which improves the ability of the detector to distinguish beads 104 having similar colors, such as lime green and mint green.

Figure 2:
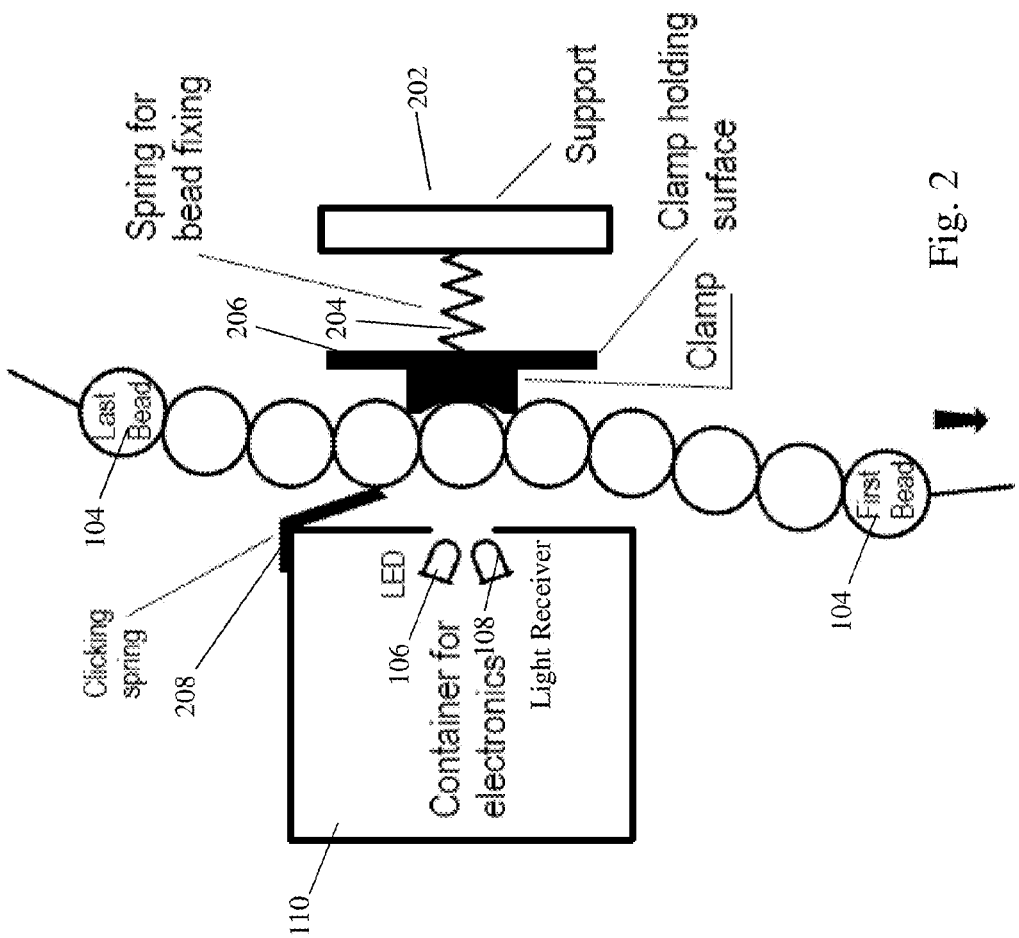
FIG. 2 illustrates an example implementation and depicts a colored object detector in accordance with the present application.

FIG. 2 illustrates an example implementation of colored object detector 100 that includes additional components not illustrated in FIG. 1. For example, the implementation illustrated in FIG. 2 includes support 202 that provides support for a spring mechanism 204 that is coupled to clamp 206. Further, the implementation shown in FIG. 2 includes clicking spring 208, support 202, spring 204 and clamp 206, which provide for increased tension while beads 104 travel (e.g., are pushed or pulled) through tube 102. One advantage of the combination of elements in colored object detector 100 that includes support 202, spring 204, clamp 206 and clicking spring 208 is that the last bead 104, such as in a strand, can be held in a fixed position temporarily during the color detection process. Fixing the last bead 104 increases an ability for the color of that bead 104 to be detected accurately by light receiver 108.

Thus, as shown in example implementations of FIGS. 1 and 2, beads 104 travel through tube 102 and a color detector that comprises, for example, light source 106 and light receiver 108 in housing 110 detects the sequence of colors set forth respectively on the beads 104. In one or more implementations, various circuitry (e.g., including a microprocessor and a communications module) is further configured with colored object detector 100 to process and communicate information associated with one or more colors (e.g., the sequence of colors) to an external device. For example, information can be communicated by flashing of an external device or a cable using a sonic connection. Accordingly, colors of each of a plurality beads can be detected using a combination of electronic components, and letters, words and/or small phrases that correspond the each of the respective color(s) of the bead(s) can be identified and communicated. Information associated with the colors can be transmitted to a display or audible module, thereby enabling respective letters, words and/or phrases that correspond with the colors to be provided (e.g., displayed on a display device). In one or more implementations, as a respective color is detected corresponding pixels are displayed that form one or more letters. For example, as a green colored bead 104 is detected, the letter L is displayed. As a blue colored bead 104 is detected, the letter M is displayed. In one or more implementation, a housing (e.g., formatted as a box) contains mechanisms for recognizing the colors of the beads and communicating information associated with the colors for corresponding letters, words and/or phrases.

Figure 3:
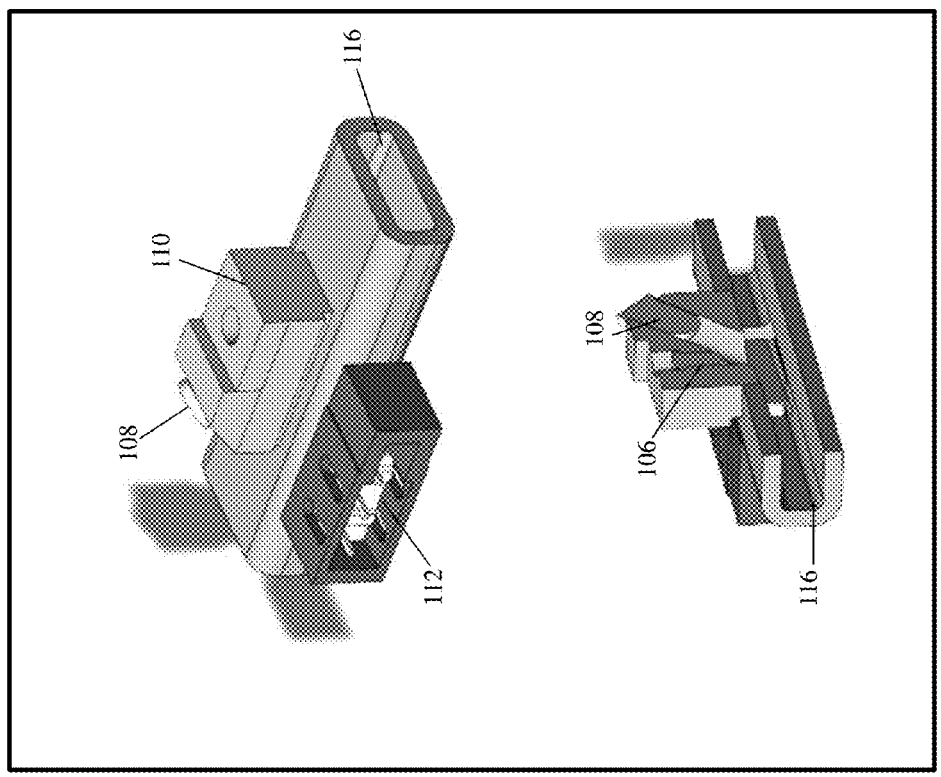
FIGS. 3-8 illustrate example assemblies in accordance with one or more implementations of the present application.
Figure 4:
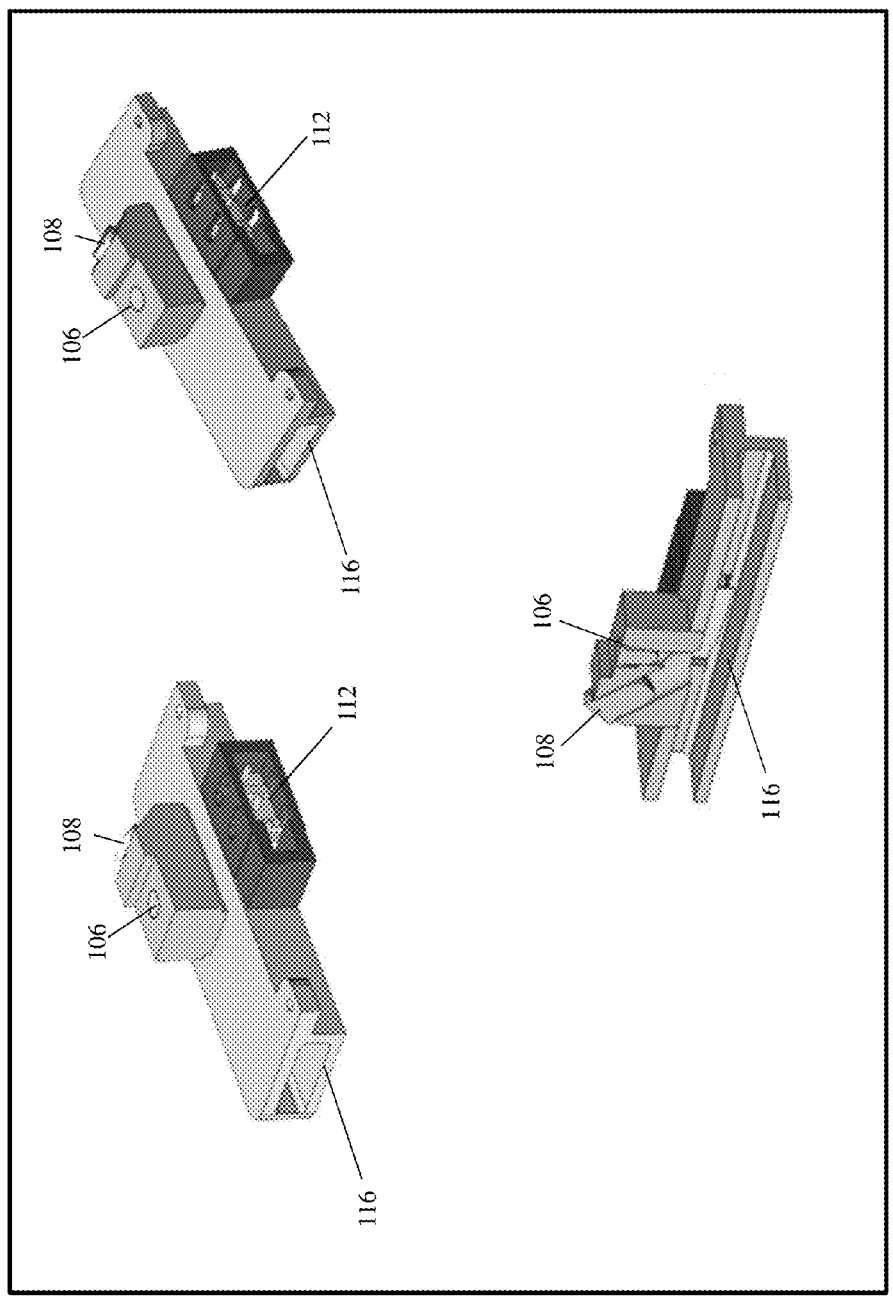
Figure 5:
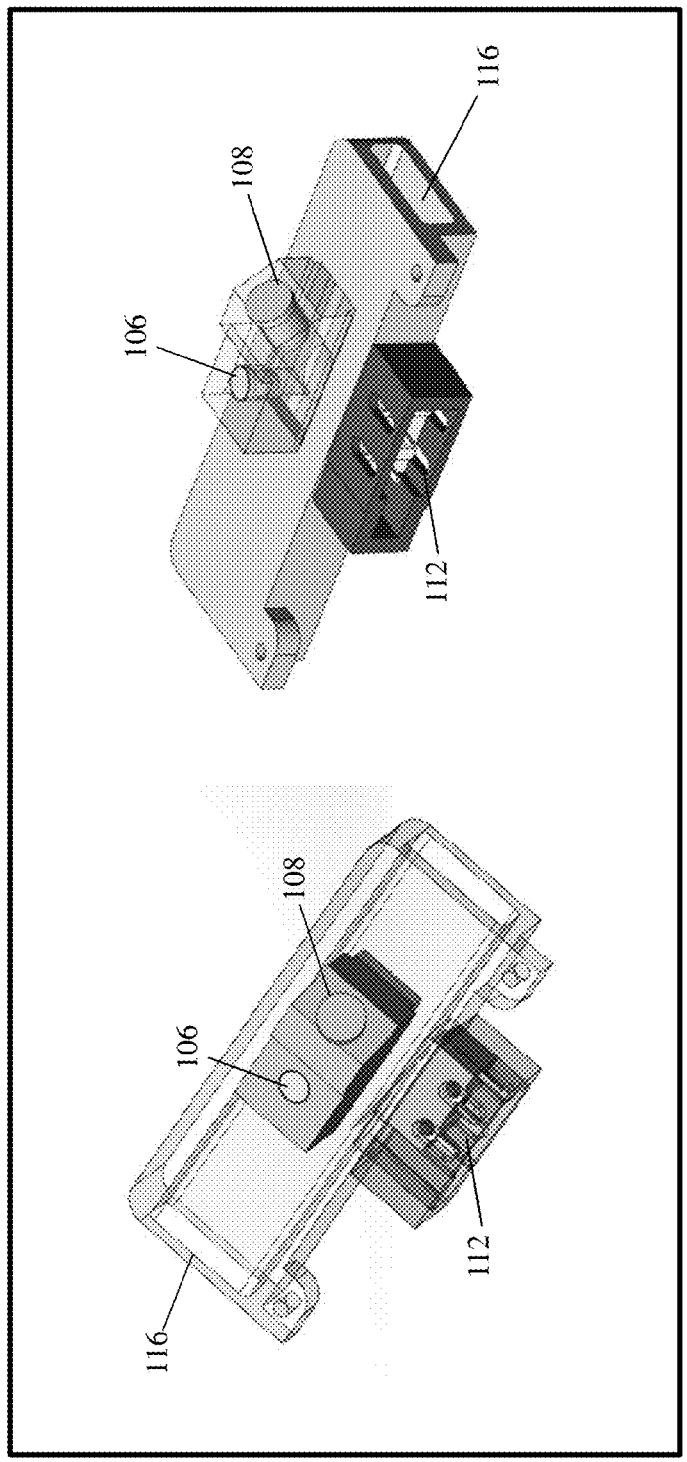
Figure 6:
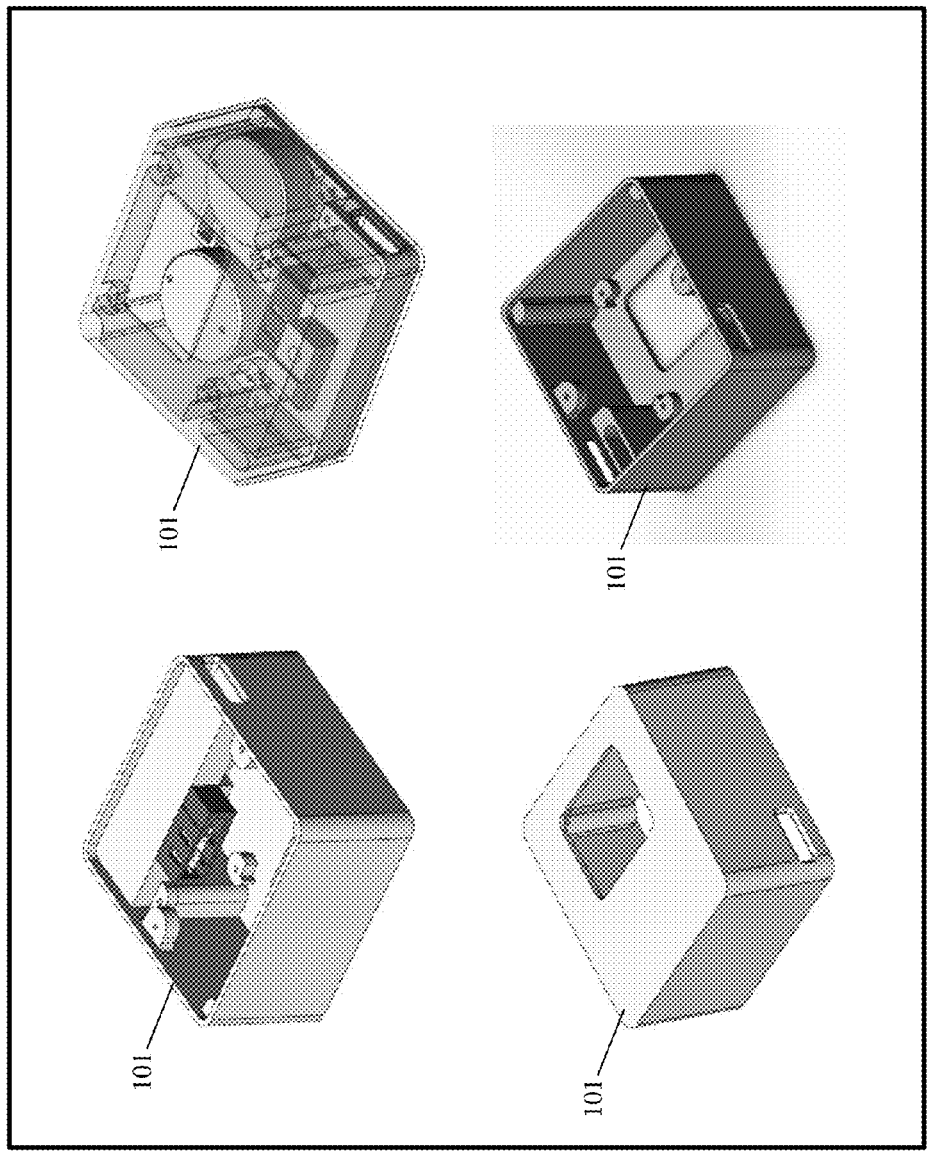
Figure 7:
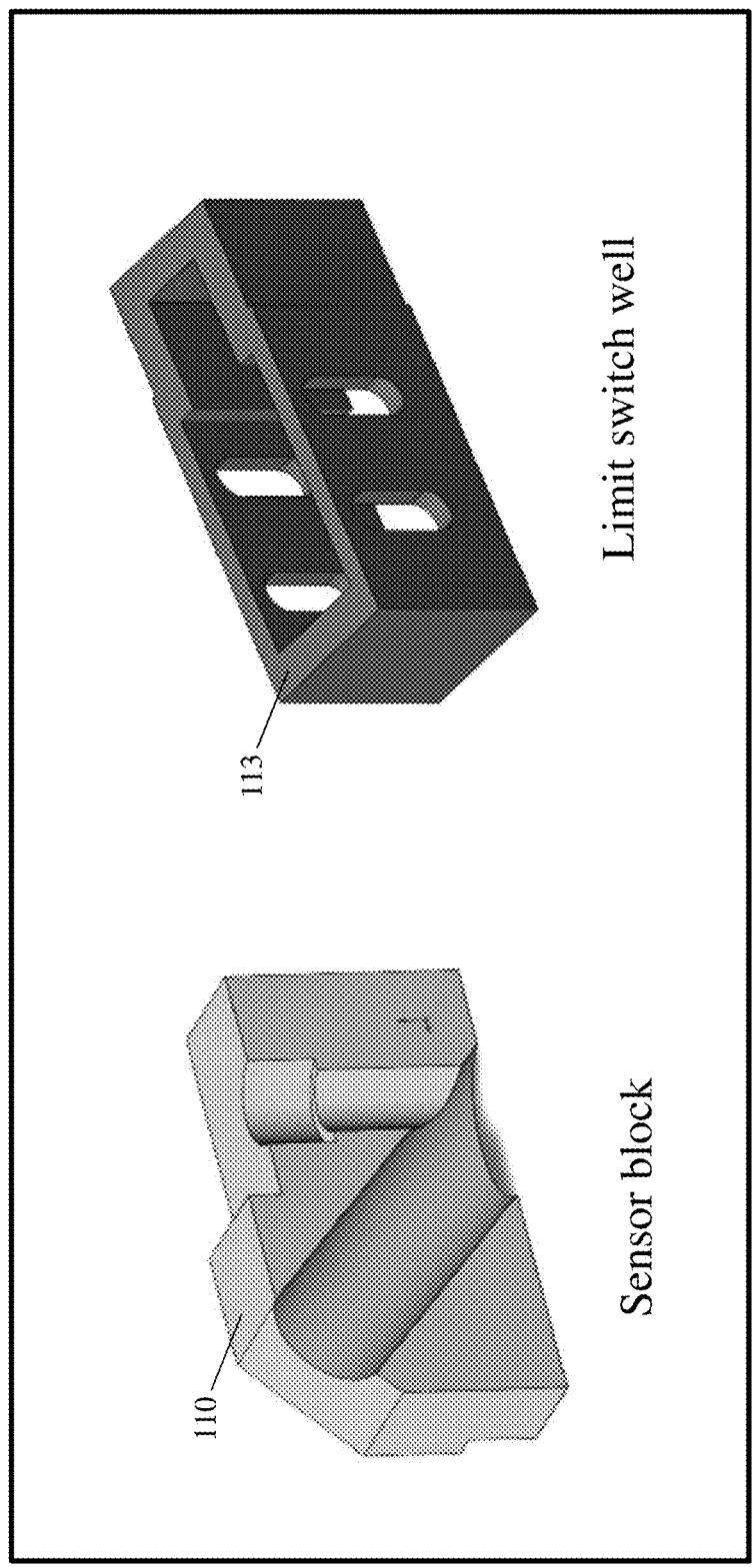
Figure 8:
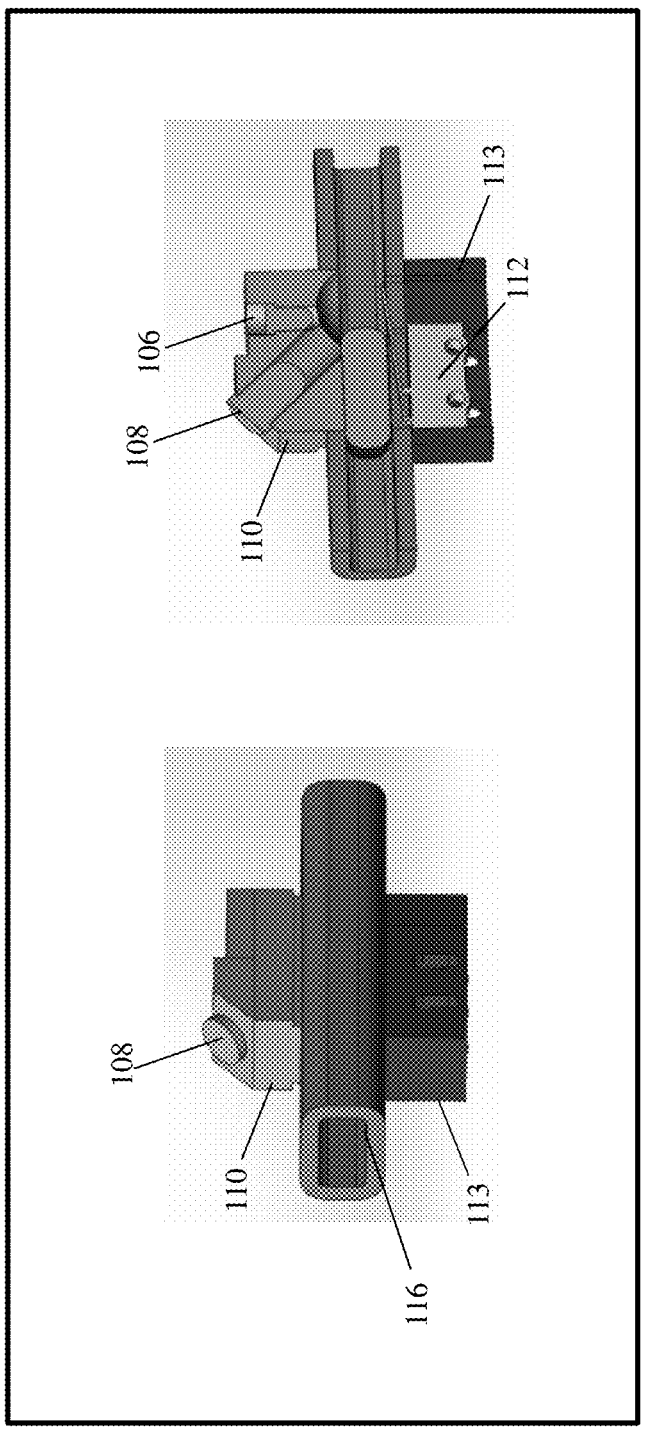

FIGS. 3-8 illustrate example implementations of the present application and include example tunnels, sensor blocks, light sources, light detectors and switches. FIG. 3, for example, illustrates an example implementation that illustrates components and an assembly that accommodate round, flat beads 104. As illustrated in FIG. 3, the tunnel 116 can be fixed in a container, such as a box, as a function of eyelets. In the example implementations illustrated in FIGS. 3-6, assemblies are provided that accommodate rectangular, flat beads 104. FIG. 6 illustrates a plurality of views of a housing assembly 101 configured as a box, for example. The example housing 101 shown in FIG. 6 is configured to support colored object detector 100. FIG. 7 illustrates a view of a sensor block 110 and limit switch well 113 in accordance with an example implementation. FIG. 8 illustrates perspective and side views of an alternative assembly for rectangular flat beads, and inclues light source 106, light receiver 108, sensor block 110, limit switch 112, limit switch well 113, and tunnel 116.

Figure 10:
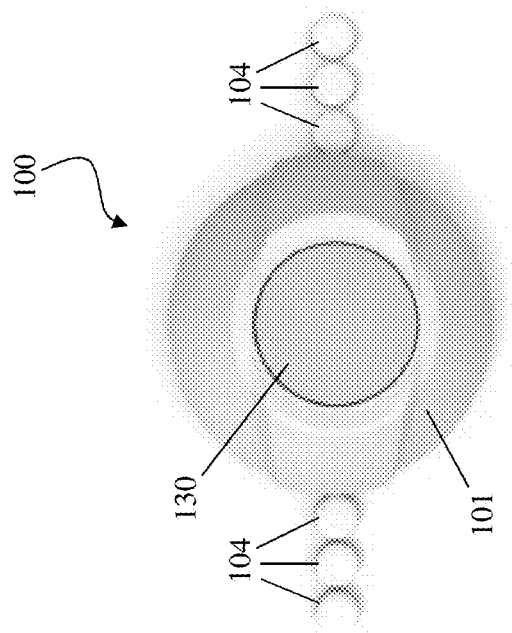
FIGS. 9 and 10 illustrate an example implementation of a colored object detector configured with a display screen that is integrated within a housing.
Figure 9:
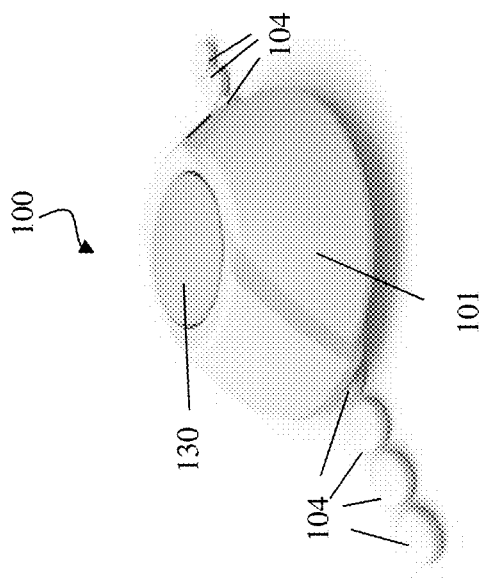

FIGS. 9 and 10 illustrate an alternative example implementation of a colored object detector 100 that is configured with a display screen 902, and that is integrated within housing 101. Display 902 can be a liquid crystal display (LCD), LED back-lit display or other suitable display.

FIG. 9 is a perspective view of detector 100, and FIG. 10 is a top view of detector 100. Although FIGS. 9 and 10 show the display screen 902 configured in a substantially round shape, display screen 902 can be formatted to be substantially circular, oval, square or rectangular (with rounded corners or right angles), triangular, diagonal, or virtually any other suitably desired shape. Thus as shown in FIGS. 3-10, a plurality of beads are each colored in one of potentially dozens of colors (e.g., 40 colors) and configured suitably for light reflection, which can be provided and capable of being detected by colored object detector 100.

It is recognized by the inventor that after a period of usage one or more batteries partially discharge and voltage drops, which may influence the brightness of the LED and/or the ability for the sensor to receive correct data. The present application includes one or more features to reduce or eliminate power voltage deviation from batteries, e.g., CR2032. In one or more implementations, a battery monitoring circuit (not shown) is included and configured to measure voltage from one or more batteries. Moreover, a data table can be maintained and referenced that stores voltage value(s) and is updated with up-to-date voltage readings. As the table data gets updated with information representing a present voltage reading, detector 100 adjusts to match the output voltage and maintain accurate color detection.

Figure 11:
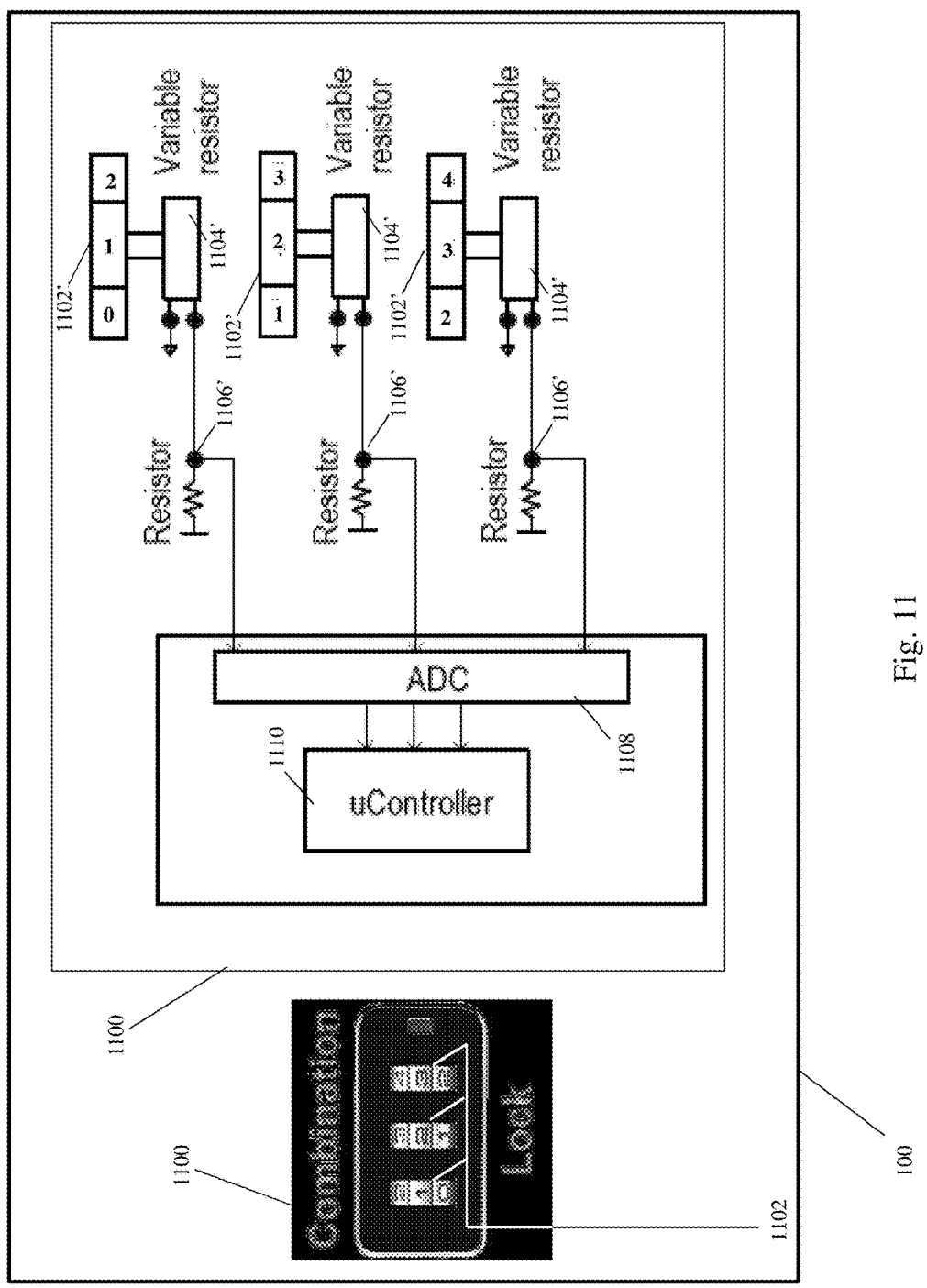
FIG. 11 illustrates an example combination lock that can be configured with a colored object detector, in accordance with an example implementation of the present application.

In one or more implementations, the present application supports a form of encryption of messages. Moreover, the present application includes features that supports virtually unlimited messages that can be coded within a single strand of colored objects (e.g., beads) in the form of colored bracelets. Colored object detector 100 can be configured with a combination lock that, when locked, precludes the display or provisioning of the letters, words or phrases that correspond with the detected colors from the bead(s) 104. FIG. 11 illustrates an example colored object detector 100 that is configured with a combination lock 1100 and corresponding hardware that interfaces with lock 1100. As shown in FIG. 11, combination lock 1100 can be configured with notched rotating discs 1102, and each respective notch corresponds to numerals in a correct combination. Furthermore, FIG. 11 illustrates an example schematic of components that interface with combination lock 1100 and that can be included in and/or accessible by colored object detector 100. In the example shown in FIG. 11, each of the rotating discs 1102' is associated with a respective variable resistor 1104'. Each respective variable resistor 1104' is operatively coupled to a respective resistor 1106', and each resistor 1106' is operatively coupled to an analog-to-digital converter (ADC) 1108. Use of components 1102', 1104' and 1106' are usable to generate a digital value that can be transmitted, for example, to a microprocessor ("uController") 1110. Employing variable resistors 1104' and resistors 1106', as shown in the example implementation illustrated in FIG. 11, enables a determination associated with the value of each respective disc 1102'. If discs 1102' are set to the proper combination (e.g., 1 2 3), then the variable resistors 1104' can cause voltage to pass to each respective resistor 1106', and cause voltage to respectively pass to the ADC 1108 and configure uController 1110 to "unlock" the colored object detector to enable detection (e.g., "reading") of letters, words, phrases and/or message(s) encoded in colored bead(s) 104. Thus, in one or more implementations of the present application, a combination security "lock" can be configured with colored object detector 100 to protect the confidentiality of encoded messages using one or more colored beads 104 and, upon entry of a correct combination, the messages can be decoded.

As noted above, a virtually unlimited number of messages can be encoded within a single strand of beads 104. In one or more implementations, for example, a single color can represent different things (e.g., letters, words, phrases, etc.) depending upon a specific numerical (or other) value or combination of values. For example, a green colored bead 104 represents the word "hello" when the combination for the lock is 1 2 3. The same green colored bead 104 represents the word "good-bye" when the combination for the lock is 4 5 6. Use of a combination lock or other coded system in this way can dramatically increase the amount of information that can be represented by one or more colored beads 104.

Figure 12:
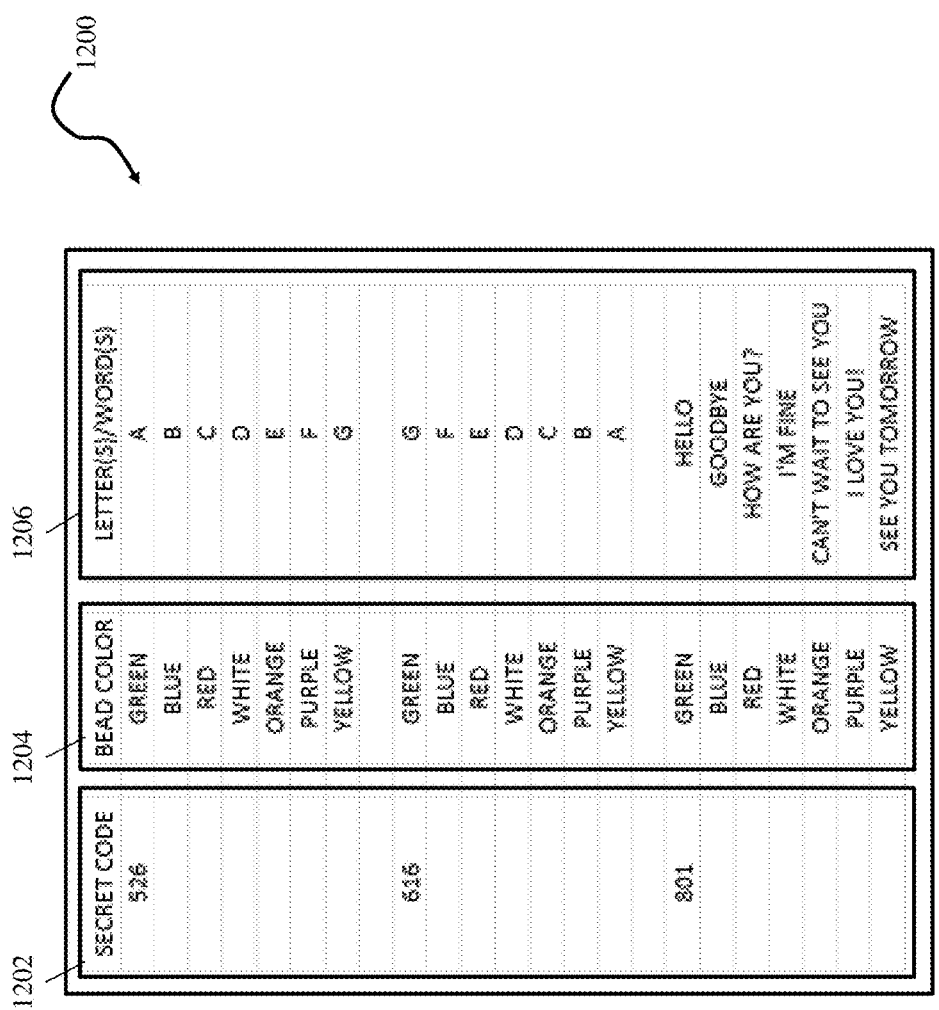
FIG. 12 illustrates an example simplified reference document showing a key of secret codes, bead colors and corresponding letters/words.

In an example implementation, a document, book, file, spreadsheet, chart or other reference can include a key of combination codes, colors and corresponding letters/words/phrases/or other suitable content. Such reference material can be identified or packaged with a plurality of colored beads 104, such as for sale. Alternatively, the reference document may be provided remotely, such as in a web site, and purchase of beads or other colored objects can include a hyperlink or other means to access the reference document for encoding secret messages in colored objects. In yet another implementation, users can generate their own reference documents that provide custom keys to unlocking secret messages encoded within one or more strands of colored beads 104. An example simplified reference document 1200 showing a key of secret codes 1202, bead colors 1204 and corresponding letters/words 1206 is illustrated in FIG. 12. As illustrated in the example document 1200, the color "GREEN" that is associated with the secret code "526" represents the letter "A," while the same color "GREEN" associated with the secret code "616" represents the letter "G." Moreover, the same color "GREEN" that is associated with the secret code "801" represents the word "HELLO." Thus, depending upon a respective secret code, a given colored object (e.g., a green bead) represents different values. Although the example document 1200 shows just a few colors 1204, dozens of colors can be provided that can exceed the number of letters in the alphabet. In one or more implementations, words, letters, numbers, images and can be represented by colored objects for each respective code.

In yet other implantations, the present application supports custom messaging functionality. For example, a user can define the values associated with each respective colored object, such as, by entering values into an interface. Values can be textual, verbal, pictorial, or the like, for example, depending upon a respective user computing device. Thus, although a guide or other reference document can be included and distributed with beads 104, in one or more implementations, custom recorded or stored values can be decoded via object detector 100 as a function of colored beads 104.

Figure 13:
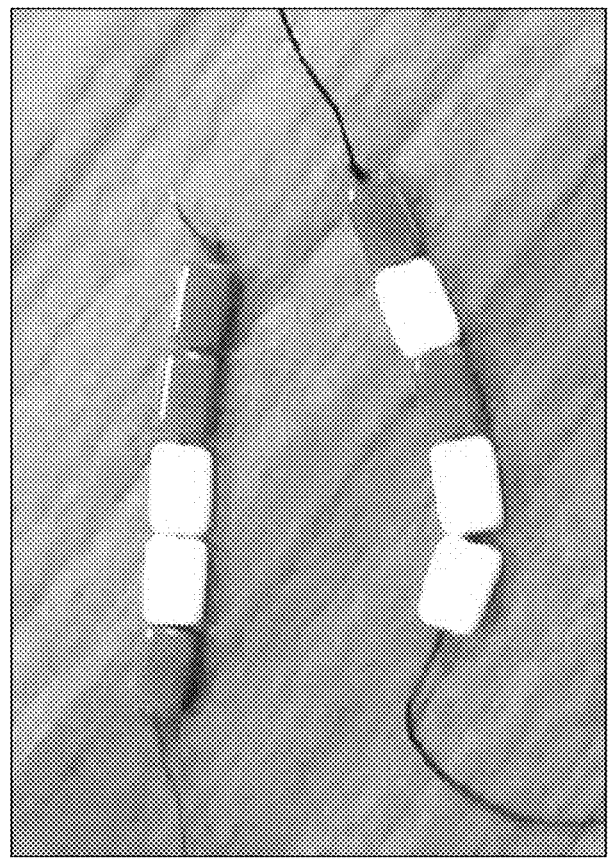
FIG. 13 illustrates example strands of colored beads that include messages that can be detected by a colored object detector, in accordance with an implementation of the present application.

For example, a consumer (e.g., a youth) purchases a package containing colored beads and a reference document that includes a key of combination codes, colors and corresponding letters/words/phrases/or other suitable content. The youth references the document and selects one of the combination codes. Thereafter, the youth strings together a respective pattern of beads into a bracelet strand, thereby "writing" a secret message. The youth then gives the bracelet to a friend and tells the friend the secret code. The friend accesses colored object detector 100, enters the combination to unlock the detector and provide a reference, and places the strand through the detector. The secret message is displayed for the friend on the display 902. FIG. 13 illustrates strands of colored beads 104 that include messages, for example, that can be detected by colored object detector 100.

Figure 14:
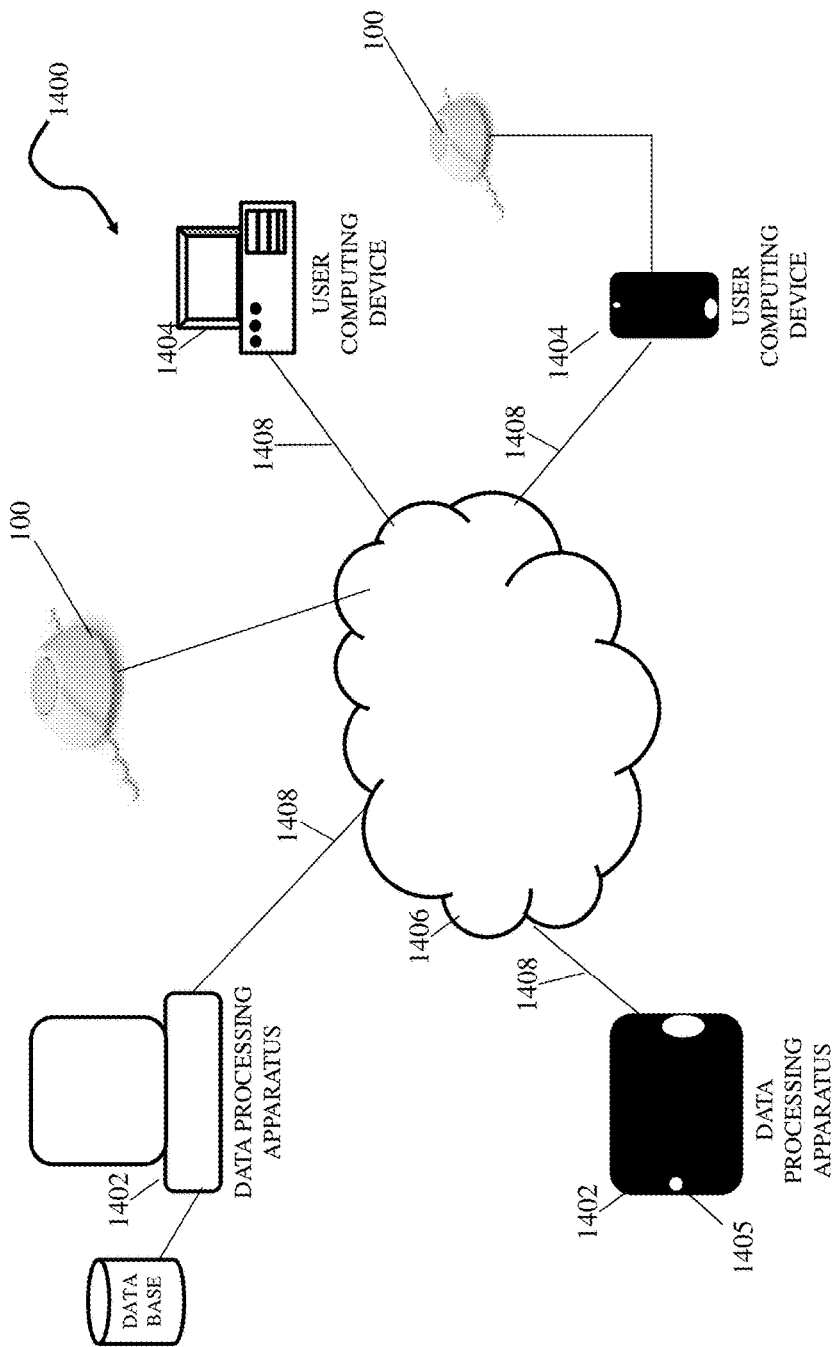
FIG. 14 is a diagram of an example hardware arrangement for providing the systems and methods disclosed herein.

Referring now to FIG. 14, an example hardware arrangement is shown that operates for providing the systems and methods disclosed herein, and designated generally as system 1400. In the implementation shown in FIG. 14, system 1400 includes one or more colored object detectors 100 that are communicatively coupled to one or more data processing apparatuses 1402 and/or user computing devices 1404 across data communication network 1406. Such colored object detector(s) 100 can be coupled to or otherwise configured with one or more communication modules for transmitting and receiving information over a communication network 1406. User computing devices 1404 can include, for example, mobile computing devices such as tablet computing devices, smartphones, personal digital assistants or the like, as well as laptop computers and/or desktop computers. Further, one computing device may be configured as a data processing apparatus 1402 and a user computing device 1404, depending upon operations be executed at a particular time. In addition, an audio/visual capture device 1405 is depicted in FIG. 14, which can be configured with one or more cameras (e.g., front-facing and rear-facing cameras), a microphone, a microprocessor, and a communications module(s) and that is coupled to data processing apparatus 1402. The audio/visual capture device 1405 can be configured to interface with one or more data processing apparatuses 1402 for producing high-quality audio/video content.

With continued reference to FIG. 14, data processing apparatus 1402 and/or user computing device 1404 can be configured to access one or more databases for the present application, including image files, video content, documents, audio/video recordings, metadata and other information. In addition, data processing apparatus 1402 can be configured to access Internet websites and other online content. It is contemplated that data processing apparatus 1402 and/or user computing device 104 can access any required databases via communication network 1406 or any other communication network to which device 1402 and/or device 1404 has access. Data processing apparatus 1402 and/or user computing device 1404 can communicate with devices including those that comprise databases, using any known communication method, including Ethernet, direct serial, parallel, universal serial bus ("USB") interface, and/or via a local or wide area network.

User computing devices 1404 communicate with data processing apparatus(es) 1402 using data connections 1408, which are respectively coupled to communication network 1406. Communication network 1406 can be any communication network, but is typically the Internet or some other global computer network. Data connections 1408 can be any known arrangement for accessing communication network 1406, such as the public internet, private Internet (e.g., VPN), dedicated Internet connection, or dial-up serial line interface protocol/point-to-point protocol (SLIPP/PPP), integrated services digital network (ISDN), dedicated leased-line service, broadband (cable) access, frame relay, digital subscriber line (DSL), asynchronous transfer mode (ATM) or other access techniques.

User computing devices 1404 can be configured to send and receive data across communication network 1406, and are equipped with web browsers, software applications, or other means, to provide received data on display devices incorporated therewith. By way of example, user computing device 1404 may be personal computers such as Intel Pentium-class and Intel Core-class computers or Apple Macintosh computers, tablets, smartphones, but are not limited to such computers. Other computing devices which can communicate over a global computer network such as palmtop computers, personal digital assistants (PDAs) and mass-marketed Internet access devices such as WebTV can be used. In addition, the hardware arrangement of the present invention is not limited to devices that are physically wired to communication network 1406, and that wireless communication can be provided between wireless devices and data processing apparatuses 1402. In one or more implementations, the present application provides improved processing techniques to prevent packet loss, to improve handling interruptions in communications, and other issues associated with wireless technology.

According to an implementation of the present application, user computing device 1404 provides user access to data processing apparatus 1402 and/or other devices for various purposes, including to control applications associated therewith and for receiving and providing information. The various functionality provided by system 1400 and, in particular, data processing apparatus(es) 1402 and user computing device(s) 1404 is described in detail below.

Devices included in system 1400 can be configured with or access software that, when executed, causes the devices to provide functionality described in greater detail herein. Such software can reside on one or more data processing apparatuses 1402, user computing devices 1404 and/or other devices. One of the functions that can be performed by data processing apparatus 1402 is that of operating as a server and/or a web site host. Data processing apparatus 1402 typically communicates with communication network 1406 across a permanent e.g., un-switched, data connection 1408. Permanent connectivity ensures that access to data processing apparatuses 1402 is always available.

Figure 15:
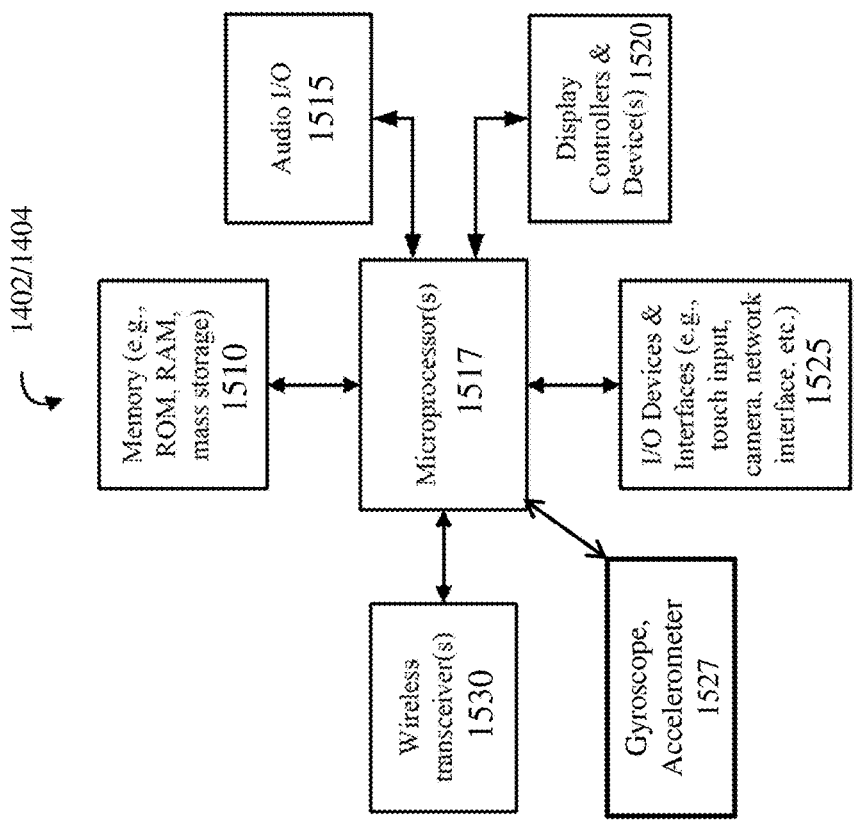
FIG. 15 illustrates, in block diagram form, an exemplary data processing apparatus and/or user computing device.
Figure 16:
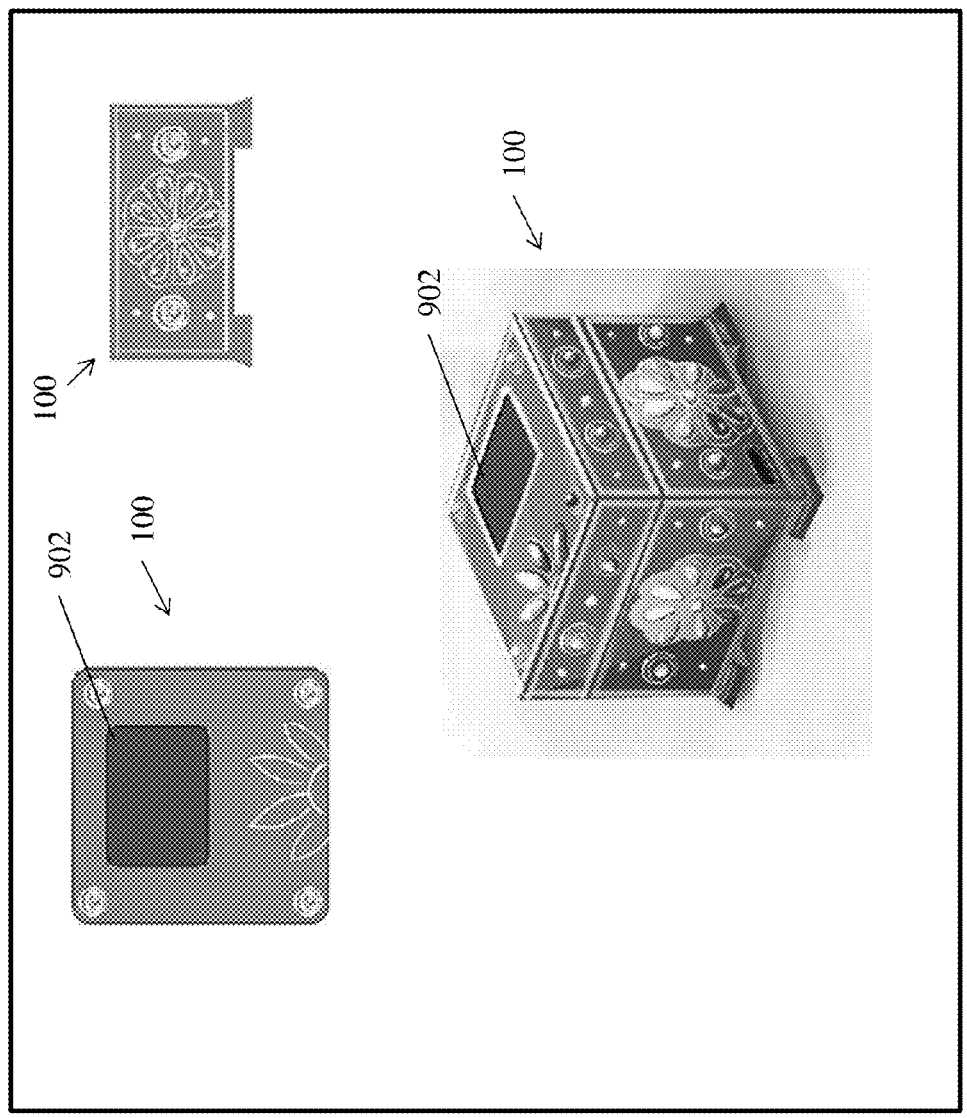
FIGS. 16-23 illustrate example implementations of colored object detectors and illustrate various example housings.
Figure 17:
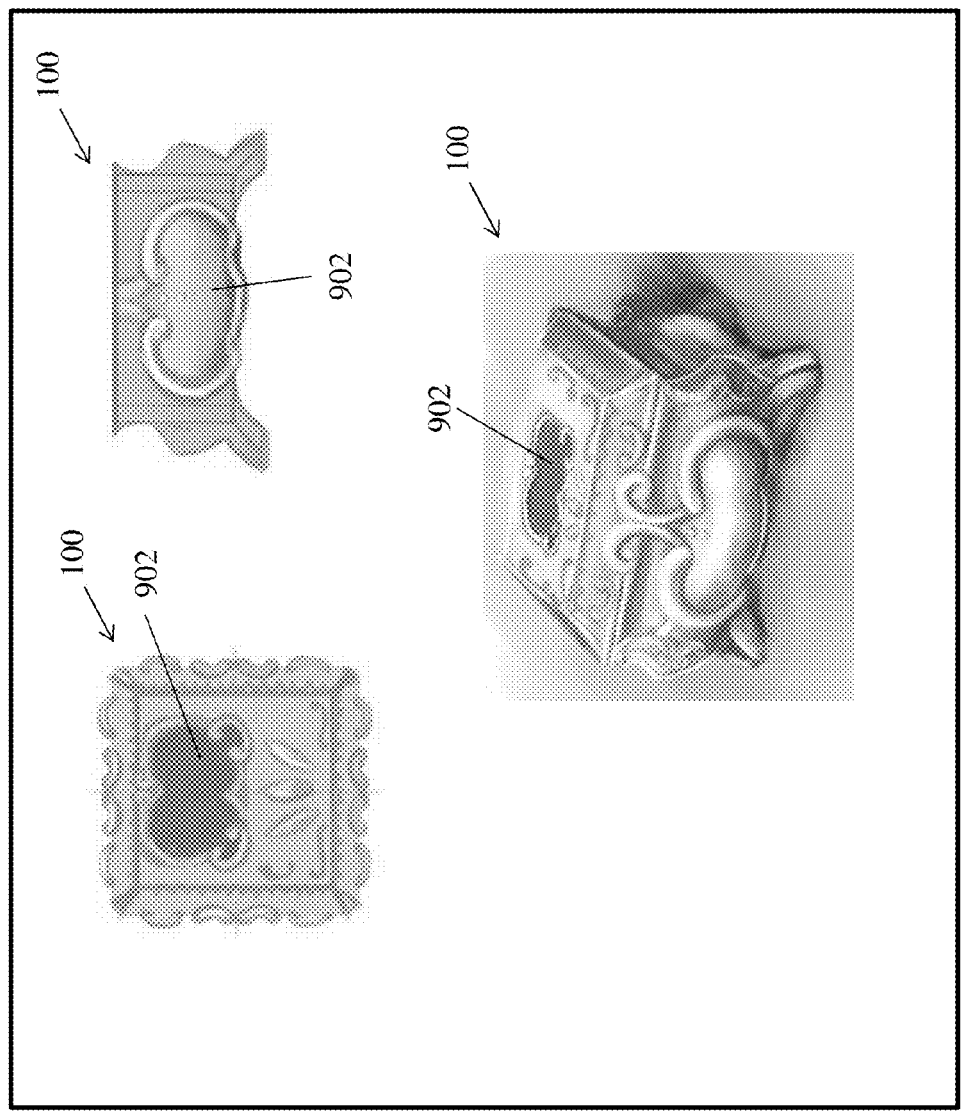
Figure 18:
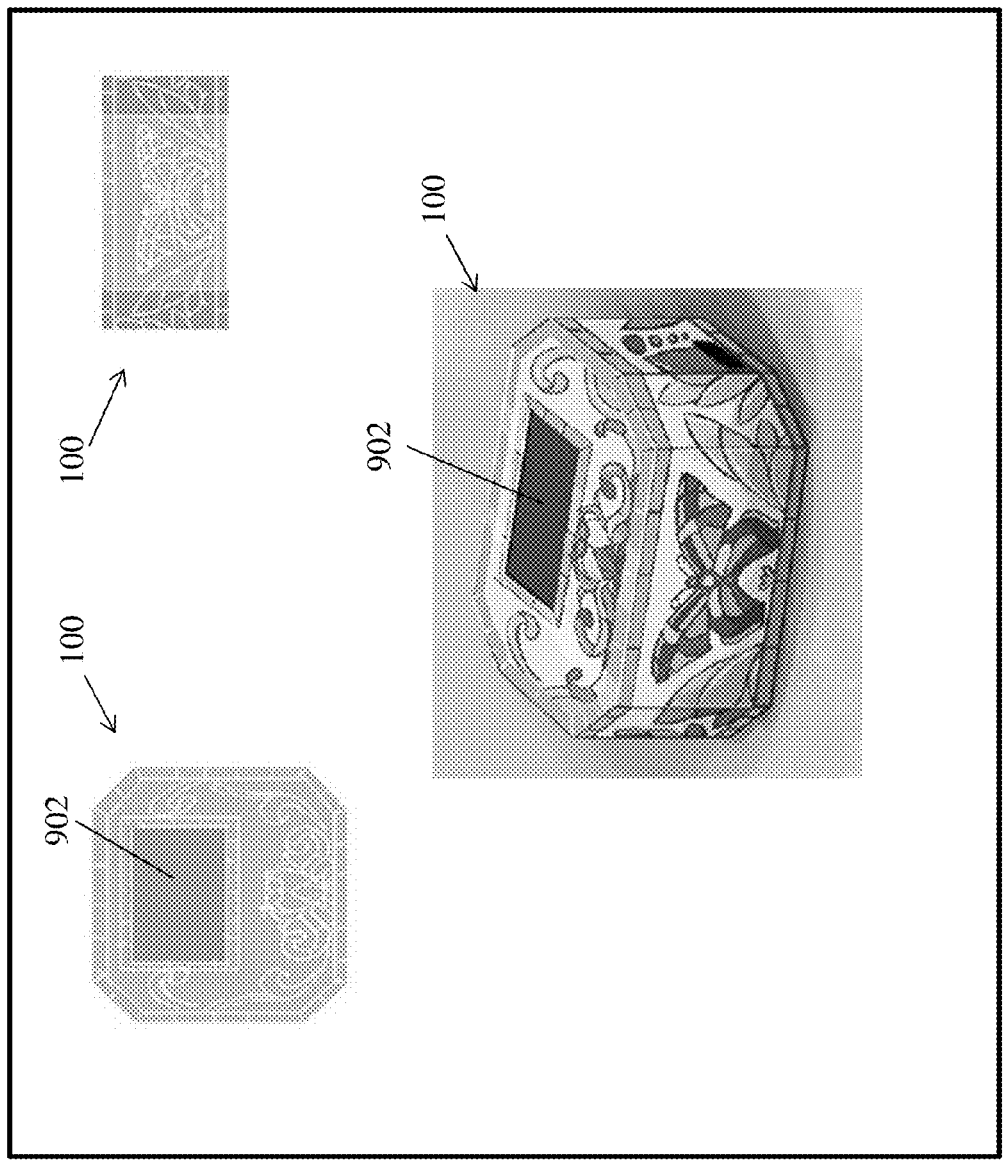
Figure 19:
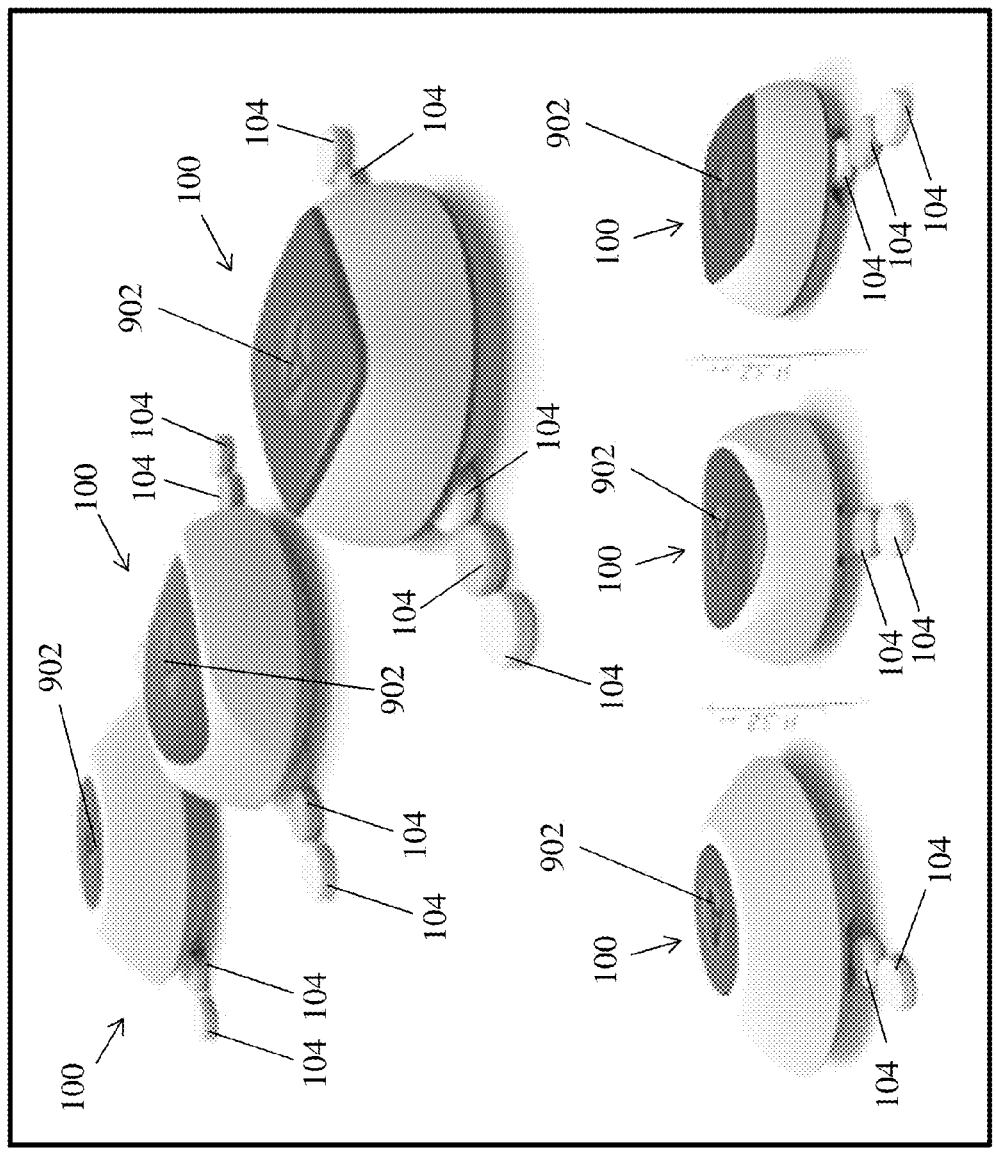
Figure 20:
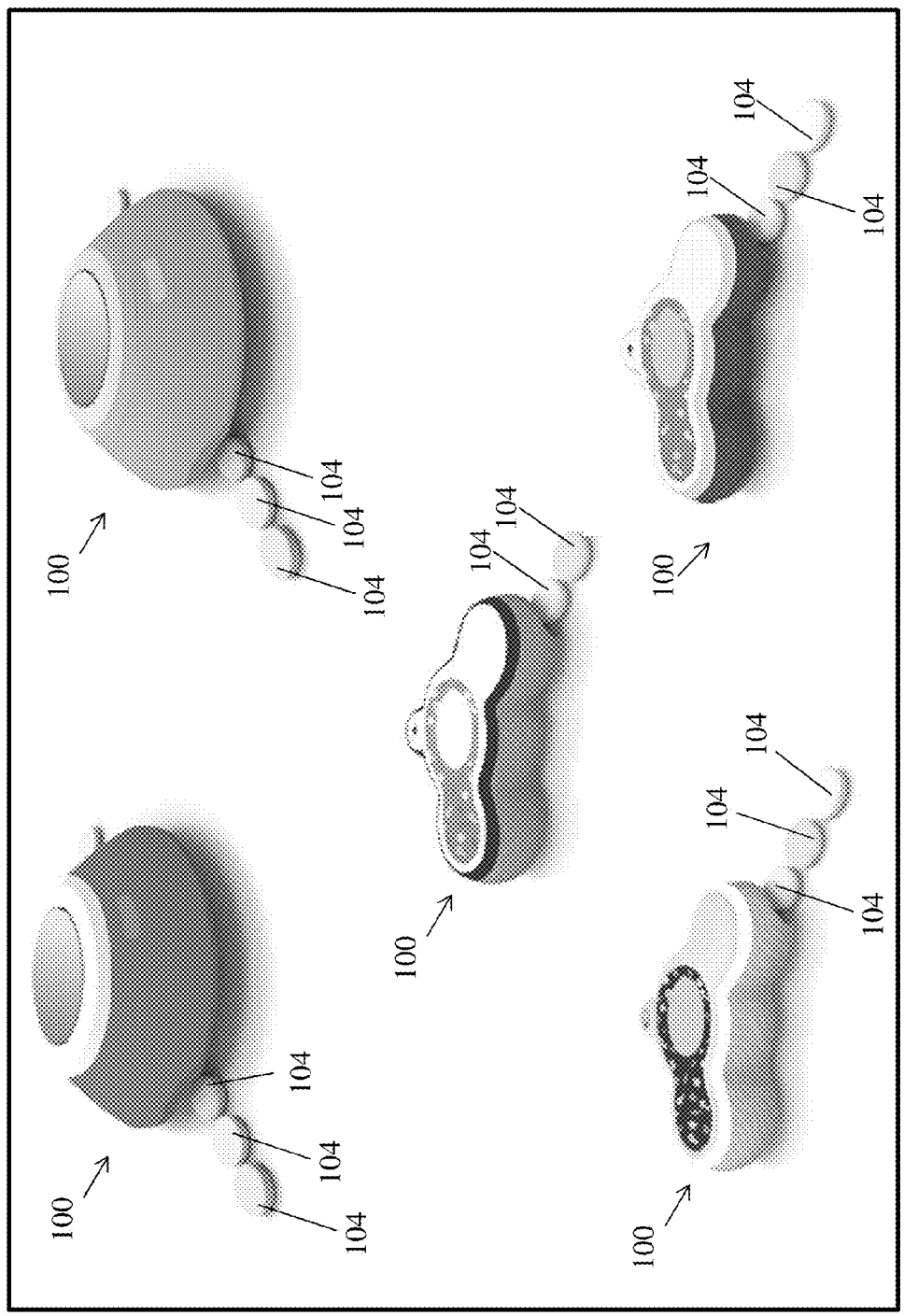
Figure 21:
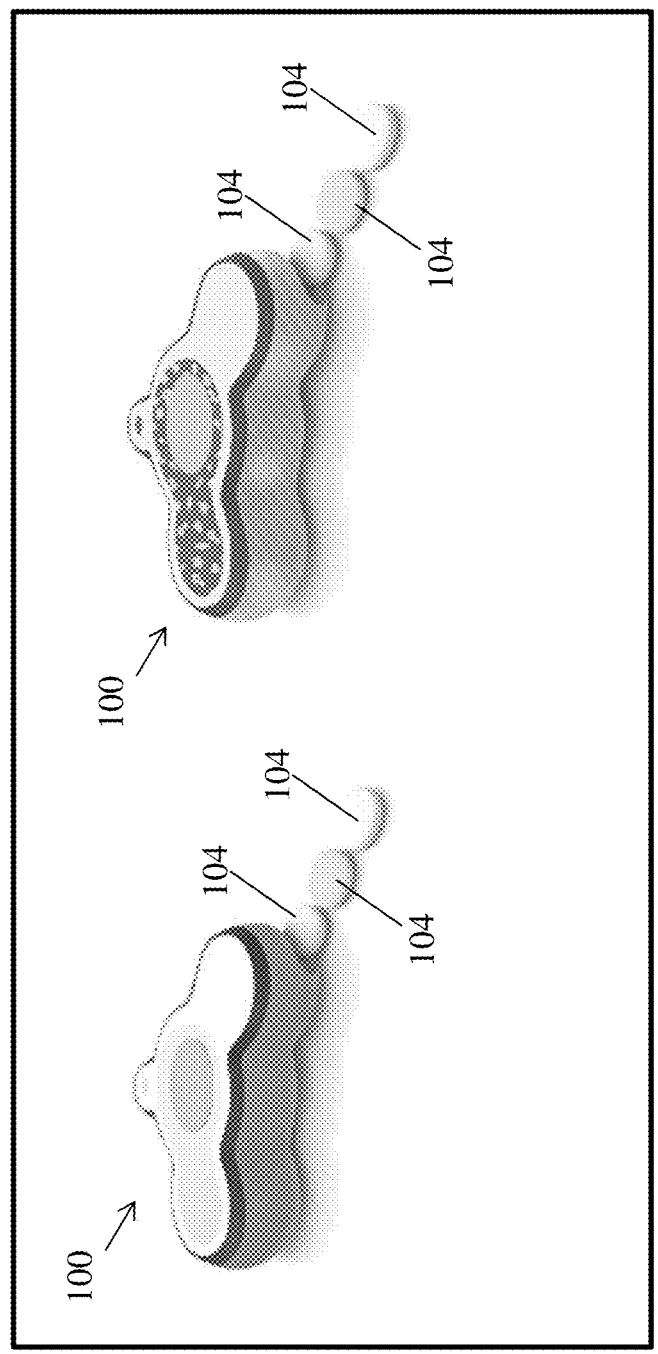
Figure 22:
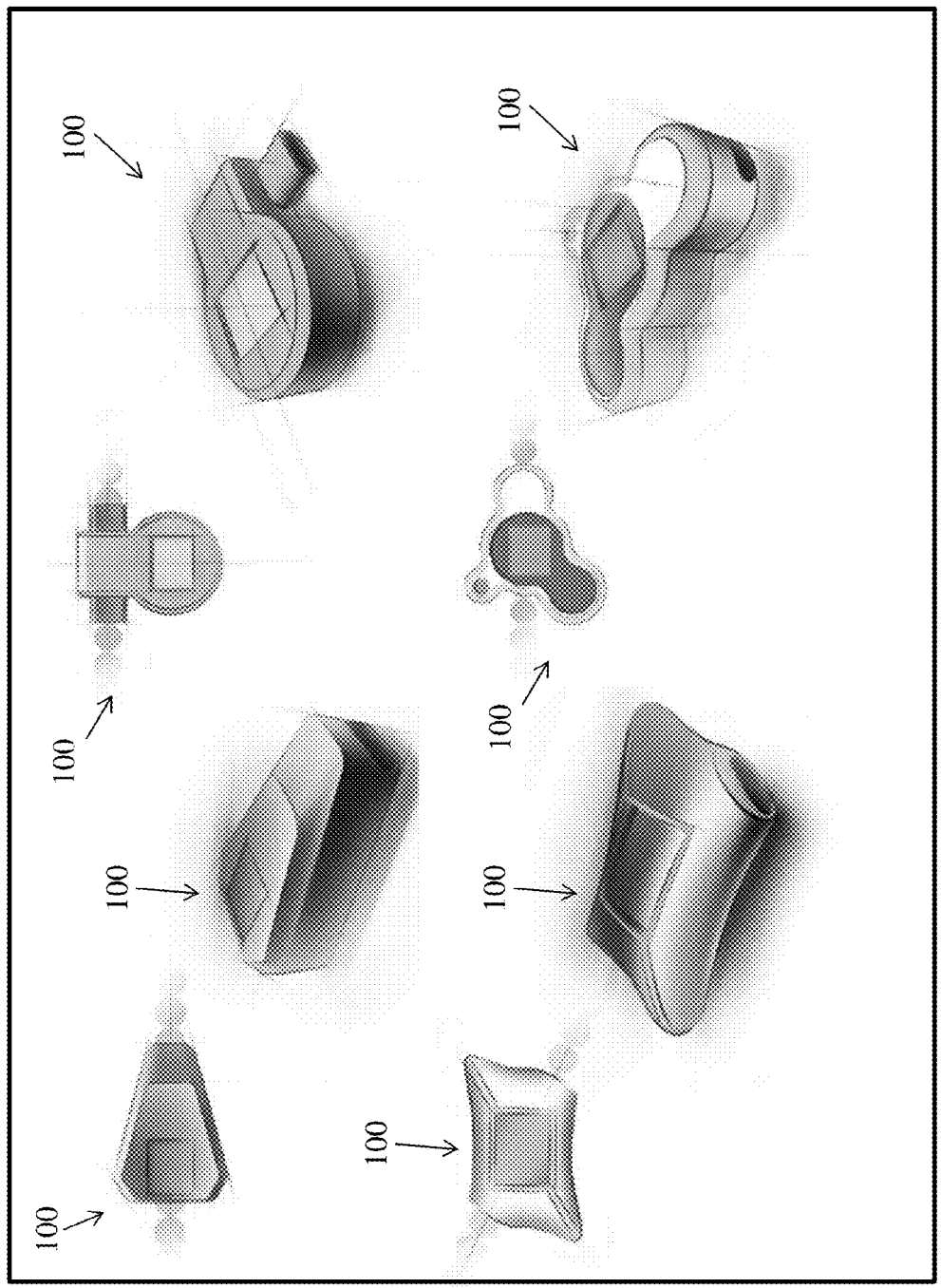
Figure 23:
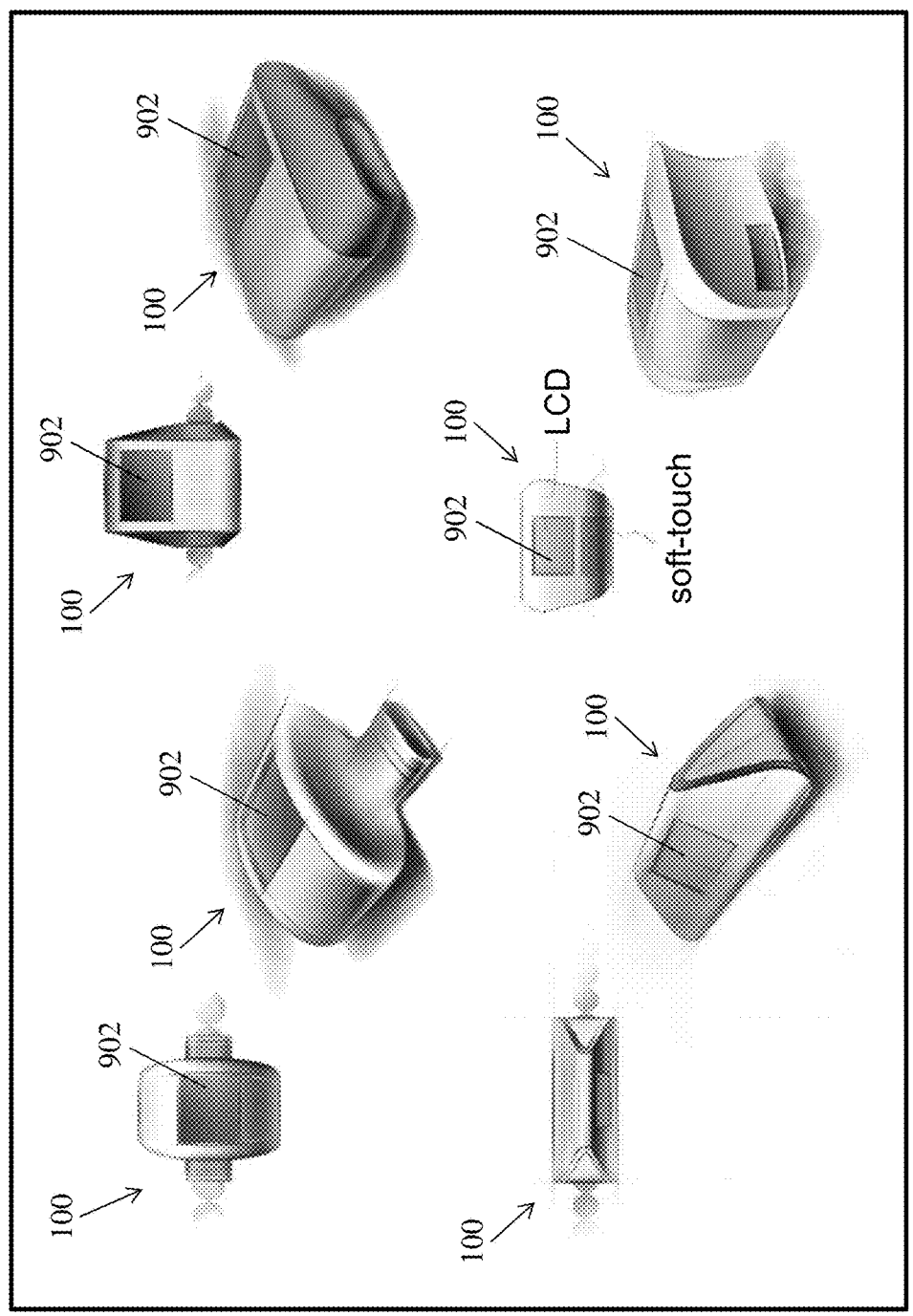
Figure 24:
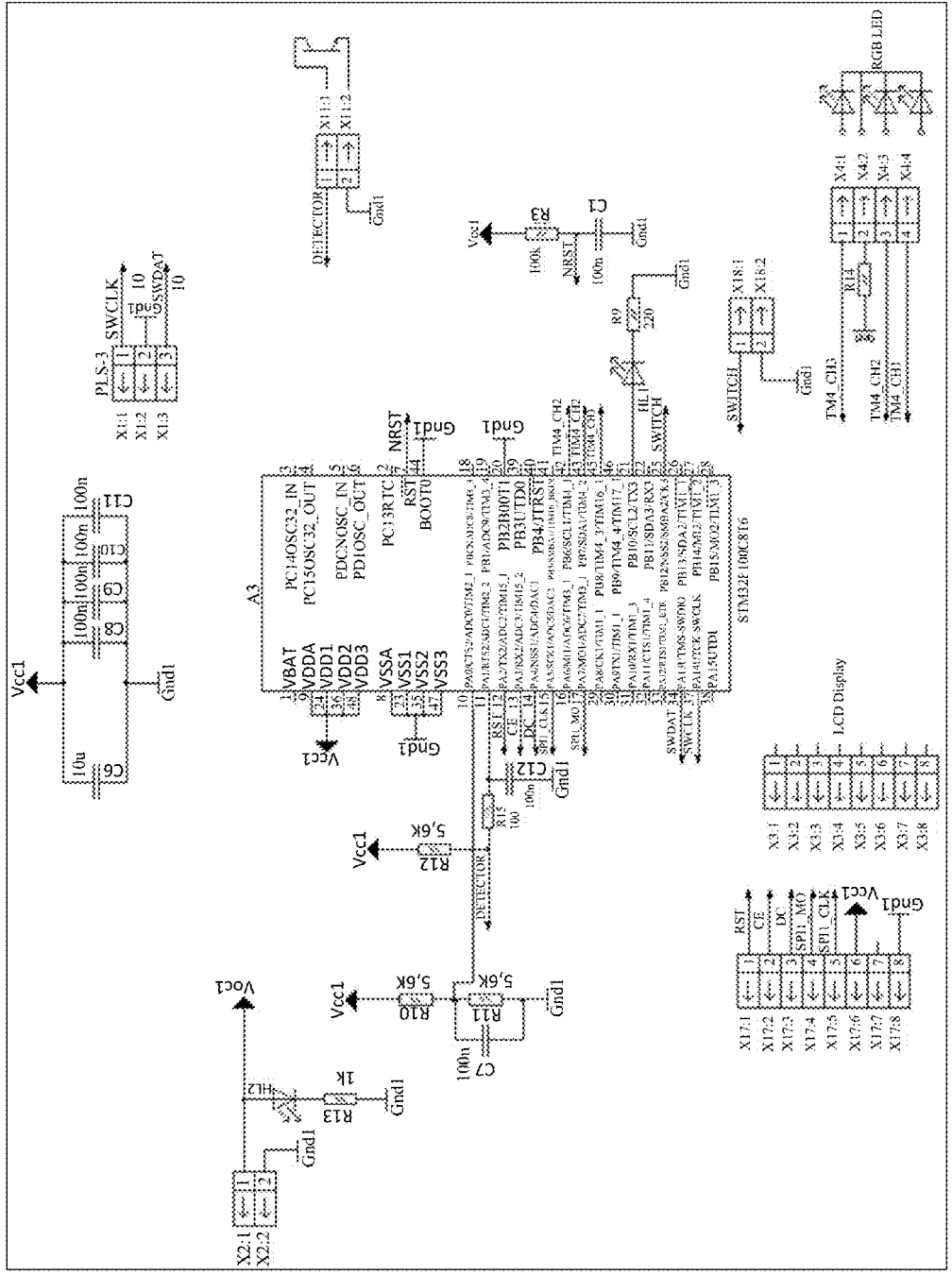
FIGS. 24-27 illustrate example schematics and circuit diagrams associated with various components and/or features of one or more colored object detectors in accordance with the present application.
Figure 25:
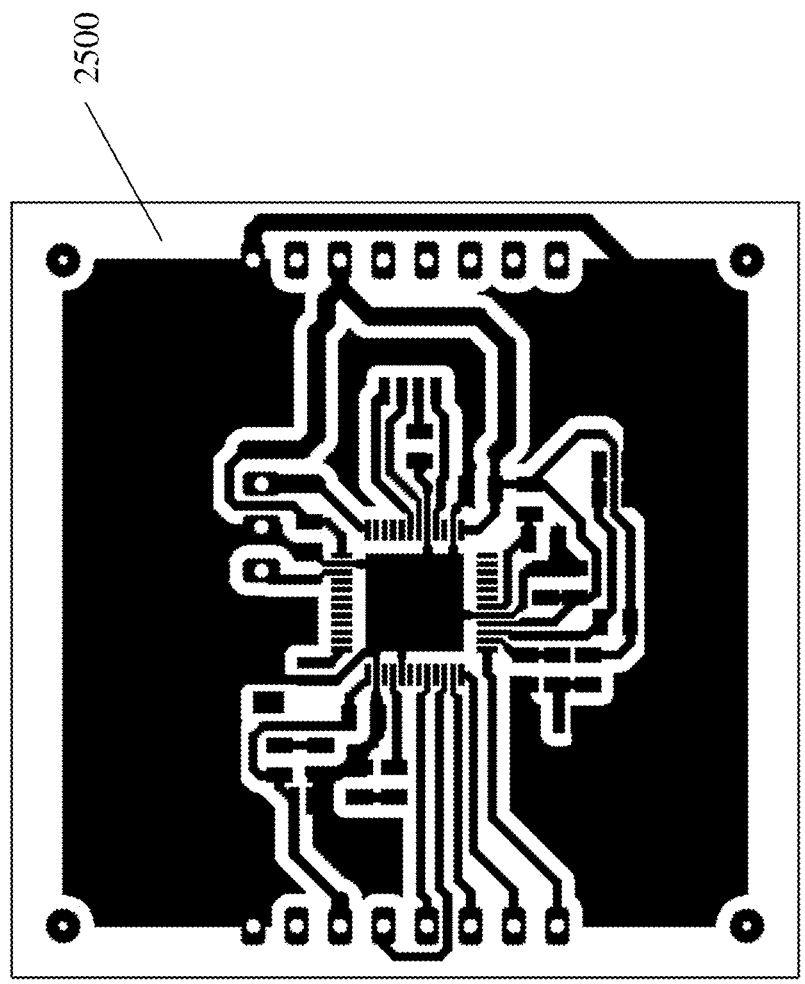
Figure 26:
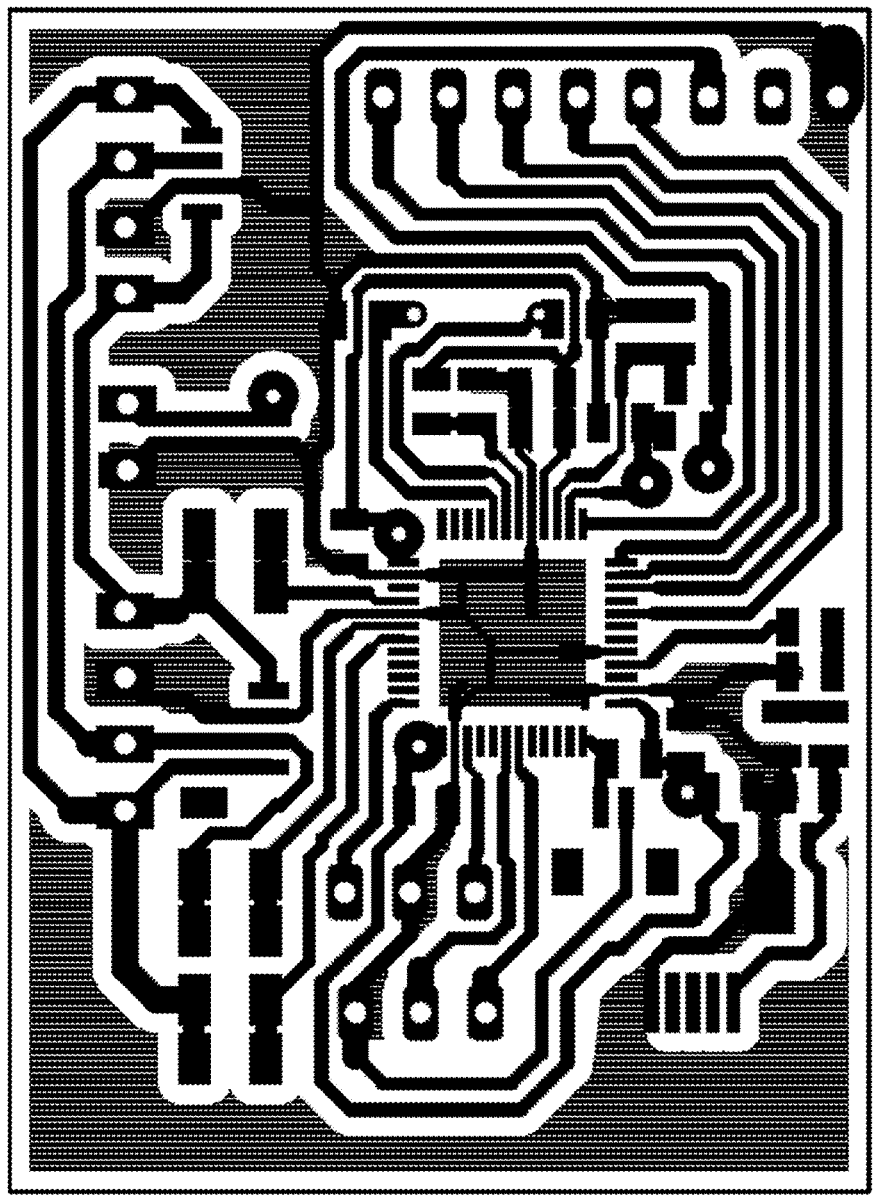
Figure 27:
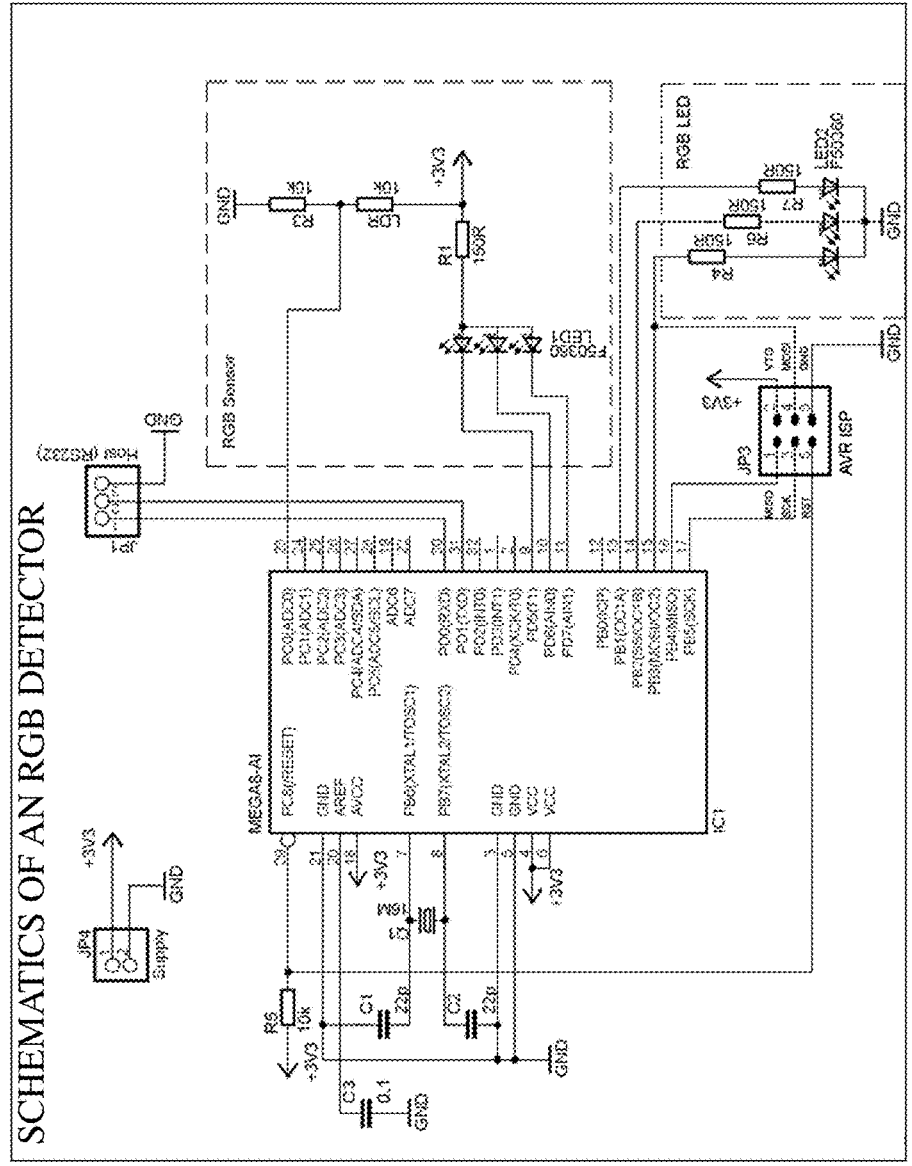

FIG. 15 illustrates, in block diagram form, an exemplary data processing apparatus 1402 and/or user computing device 1404 that can provide functionality in accordance with the teachings herein. Although not expressly indicated, one or more features shown and described with reference with FIG. 15 can be included with or in the audio/visual capture device 1405, as well as colored object detector 100. Data processing apparatus 1402, user computing device 1404 and/or colored object detector 100 may include one or more microprocessors 1517 and connected system components (e.g., multiple connected chips) or the data processing apparatus 1402 and/or user computing device 1404 may be a system on a chip.

The data processing apparatus 1402 and/or user computing device 1404 includes memory 1510 which is coupled to the microprocessor(s) 1517. The memory 1510 may be used for storing data, metadata, and programs for execution by the microprocessor(s) 1517. The memory 1510 may include one or more of volatile and non-volatile memories, such as Random Access Memory ("RAM"), Read Only Memory ("ROM"), Flash, Phase Change Memory ("PCM"), or other type.

The data processing apparatus 1402 and/or user computing device 1404 can also include an audio input/output subsystem 1515 which may include a microphone and/or a speaker for, for example, playing back music, providing telephone or voice/video chat functionality through the speaker and microphone, or the like.

A display controller and display device 1520 provides a visual user interface for the user; this user interface can include a graphical user interface which, for example, is similar to that shown on a Macintosh computer when running Mac OS operating system software or an iPad, iPhone, or similar device when running iOS operating system software.

The data processing apparatus 102 and/or user computing device 104 also includes one or more wireless transceivers 1530, such as an IEEE 802.11 transceiver, an infrared transceiver, a Bluetooth transceiver, a wireless cellular telephony transceiver (e.g., 1G, 2G, 3G, 4G), or another wireless protocol to connect the data processing system 100 with another device, external component, or a network. In addition, Gyroscope/Accelerometer 235 can be provided Moreover, one or more buses, can be used to interconnect the various modules in the block diagram shown in FIG. 15. The data processing apparatus 1402 and/or user computing device 1404 may be a personal computer, tablet-style device, such as an iPad, a personal digital assistant (PDA), a cellular telephone with PDA-like functionality, such as an iPhone, a Wi-Fi based telephone, a handheld computer which includes a cellular telephone, a media player, such as an iPod, an entertainment system, such as a iPod touch, or devices which combine aspects or functions of these devices, such as a media player combined with a PDA and a cellular telephone in one device. In other embodiments, the data processing apparatus 1402 and/or user computing device 1404 may be a network computer or an embedded processing apparatus within another device or consumer electronic product.

The data processing apparatus 1402 and/or user computing device 1404 also includes one or more input or output ("I/O") devices and interfaces 1525 which are provided to allow a user to provide input to, receive output from, and otherwise transfer data to and from the system. These I/O devices may include a mouse, keypad or a keyboard, a touch panel or a multi-touch input panel, camera, network interface, modem, other known I/O devices or a combination of such I/O devices. The touch input panel may be a single touch input panel which is activated with a stylus or a finger or a multi-touch input panel which is activated by one finger or a stylus or multiple fingers, and the panel is capable of distinguishing between one or two or three or more touches and is capable of providing inputs derived from those touches to the data processing apparatus 1402 and/or user computing device 1404. The I/O devices and interfaces 1525 may include a connector for a dock or a connector for a USB interface, FireWire, etc., to connect with another device, external component, or a network. Moreover, the I/O devices and interfaces can include gyroscope and/or accelerometer 1527, which can be configured to detect 3-axis angular acceleration around the X, Y and Z axes, enabling precise calculation, for example, of yaw, pitch, and roll. The gyroscope and/or accelerometer 1527 can be configured as a sensor that detects acceleration, shake, vibration shock, or fall of a device 1402/1404, for example, by detecting linear acceleration along one of three axes (X, Y and Z). The gyroscope can work in conjunction with the accelerometer, to provide detailed and precise information about the device's axial movement in space. More particularly, the 3 axes of the gyroscope combined with the 3 axes of the accelerometer enable the device to recognize approximately how far, fast, and in which direction it has moved to generate telemetry information associated therewith, and that is processed to generate coordinated presentations, such as shown and described herein.

Additional components, not shown, can also be part of the data processing apparatus 1402 and/or user computing device 1404, and, in certain implementations, fewer components than that shown in FIG. 14 may also be used in data processing apparatus 1402 and/or user computing device 1404. Furthermore, and as described herein, computer-implemented methods may be carried out in a computer or other data processing system in response to its processor or processing system executing sequences of instructions contained in a memory, such as memory 1510 or other machine-readable storage medium. The software may further be transmitted or received over a network (not shown) via a network interface device 1525. In various implementations, hardwired circuitry may be used in combination with the software instructions to implement the present implementations. Thus, the techniques are not limited to any specific combination of hardware circuitry and software, or to any particular source for the instructions executed by the data processing apparatus 102 and/or user computing device 104.

As noted herein, implementations of the present application are well-suited for game-play and/or entertainment. Housing 101 can be formatted in a variety of ways, including as a toy that be attractive for youth (e.g., pre-teenage boys or girls). Of course, housing 101 can be formatted in many other ways, including in a unisex format and/or in formats that are designed to be attractive for various demographics. FIGS. 16-23 illustrate example implementations of colored object detector 100 and illustrate various example housings 101. In the implementation shown in FIGS. 16-23, housings 101 are configured with display 902 to provide text/graphical information to a user in response to a detected colored object. Further, housing 101 can be configured with audio components (e.g., microphone and/or speaker(s)), batteries, and other electronic and mechanical components for providing functionality (not shown). For example, housing 101 can be configured with one or more microprocessors, processor-readable memory communication components (e.g., Wi-Fi and/or near field communication) for providing computing processing and functionality. Colors that are detected on colored objects 104 can be used to assign one or more commands or instructions to be issued, such as in connection with displaying and/or transmitting a message or an instruction to be executed by one or more processors.

FIGS. 24-27 illustrate example schematics and circuit diagrams associated with various components and/or features of one or more colored object detectors 100, in accordance with the present application.

Thus, as shown and described herein, a system and method are provided for detecting colors, for example, on beads and one or more messages can be detected as a function thereof. Various components can include, for example, a support for a spring mechanism that is coupled to clamp. A clicking spring can be provided that, together with the support, spring and clamp, provides for increased tension while beads are pulled through a tube. As each bead travels through the tube, its color and the sequence of colors of a plurality of beads is read and can be communicated to an external device, for example, via flashing of an external device or a cable using a sonic connection. Accordingly, using a combination of electronic components, colors of a plurality beads are detected, and letters, words and/or small phrases that correspond the color(s) of the bead(s) can be identified and provided (e.g., displayed on a display device). In one or more implementation, a housing (e.g., formatted in a box) contains mechanisms for recognizing the colors of the beads and communicating information associated with the colors for corresponding letters, words and/or phrases.

The systems and methods are not limited in any way to the illustrated embodiments and/or arrangements as the illustrated embodiments and/or arrangements described below are merely exemplary of the systems and methods, which can be embodied in various forms. Therefore, it is to be understood that any structural and functional details disclosed herein are not to be interpreted as limiting the systems and methods, but rather are provided as a representative embodiment and/or arrangement for teaching one skilled in the art one or more ways to implement the systems and methods.

Although the present application has been described in relation to particular embodiments thereof, other variations and modifications and other uses are included herein. It is preferred, therefore, that the present invention not be limited by the specific disclosure herein.

What is claimed:

1. A system for detecting colored objects and decoding messages, the system comprising:
   a support;
   a spring mechanism coupled to the support;
   a clamp mechanism coupled to the support and the spring mechanism;
   a power source coupled to the support;
   a light source operatively coupled to the power source for emitting light on a colored object;
   a light receiver configured to receive the emitted light from the light source as the light reflects off the colored object and further configured to detect color of the reflected light;

a processor operatively coupled to processor readable media and configured to receive, via a communications module, information representing the color of the reflected light; and a housing, configured for supporting the light source, the light receiver, the processor and the communications module, wherein the colored object is fixed in place as a function of the spring mechanism and the clamp mechanism, thereby providing stability as the colored bead reflects the light emitted from the light source, further wherein the processor is further configured to process the information representing the color of the reflected light and provide at least partial message information corresponding to the color.

2. The system of claim 1, further comprising:
a switch configured to turn the light source on as a function of the colored object making contact with a point of the switch and to turn the light source off as a function of the colored object leaving the point of the switch.

3. The system of claim 1, further comprising:
a tube provided in the housing and configured to receive the colored object.

4. The system of claim 3, wherein the colored object is a shaped bead that travels through the tube, contacts the point of the switch, and reflects the light from the light source.

5. The system of claim 4, wherein the shaped bead is one of a strand of a plurality of respectively colored beads.

6. The system of claim 5, further comprising a tunnel containing the tube, wherein the tunnel is configured to block ambient light.

7. The system of claim 1, further comprising an output device for providing the message information.

8. The system of claim 7, wherein the output device is a display device and/or an audio output device.

9. The system of claim 1, further comprising a lock mechanism configured to preclude the message information from being provided until a value is received.

10. The system of claim 9, wherein the lock mechanism is configured as a combination lock and further comprises:
a plurality of respective resistors that, upon positioning the combination lock in accordance with the value, enables passage of voltage for providing the message information.

11. The system of claim 9, wherein the message information corresponds at least in part to the value.

12. The system of claim 11, wherein a plurality of values respectively correspond to a plurality of respective message information corresponding with the respective color.

13. The system of claim 1, wherein the light source includes a red, blue and green light emitting diode.

14. The system of claim 1, wherein the light receiver includes at least one of a photodiode, a photocell and a photo resistor.

15. A method for detecting colored objects and decoding messages, the system comprising:
emitting, by a light source operatively coupled to a power source, light on a colored object;
receiving, by a light receiver, the emitted light from the light source as the light reflects off the colored object;
detecting, by the light receiver, color of the reflected light;
receiving, by a processor operatively coupled to processor readable media, via a communications module, information representing the color of the reflected light; and
a housing, configured for supporting the light source, the light receiver, the processor and the communications module;
turning on, by a switch, the light source on as a function of the colored object making contact with a point of the switch;
turning off, by the switch, the light source as a function of the colored object leaving the point of the switch; and
processing, by the processor, information representing the color of the reflected light to provide at least partial message information corresponding to the color.

16. The method of claim 15, wherein the colored object is a shaped bead that travels through a tube, contacts the point of the switch, and reflects the light from the light source.

17. The method of claim 16, wherein the shaped bead is one of a strand of a plurality of respectively colored beads.

18. The method of claim 15, further comprising:
precluding, by a lock mechanism, the message information from being provided until a value is received, wherein the lock mechanism is configured as a combination lock that comprises a plurality of respective resistors that, upon positioning the combination lock in accordance with the value, enables passage of voltage for providing the message information.

* * * * *